United States Patent [19]

Clarke et al.

[11] Patent Number: 5,053,331

[45] Date of Patent: Oct. 1, 1991

[54] SELF-INCOMPATIBILITY GENE

[75] Inventors: Adrienne Clarke, Parkville; Shaio Lim Mau, Wheelers Hill; Marilyn Anderson, Sunbury; Edwina Cornish, Carlton, all of Australia; Hugh D. Niall, San Francisco, Calif.; Geoffrey W. Tregear, Hawthron; Robert J. Crawford, Templestowe, both of Australia; Robert Bernatzky, New Salem, Mass.

[73] Assignee: Lubrizol Genetics, Inc., Wickliffe, Ohio

[21] Appl. No.: 198,781

[22] Filed: May 25, 1988

Related U.S. Application Data

[63] Continuation-in-part of Ser. No. 854,139, Apr. 21, 1986, abandoned, which is a continuation-in-part of Ser. No. 792,435, Oct. 29, 1985, abandoned.

[51] Int. Cl.$^5$ .................... C12N 15/00; C12N 1/00; C07H 21/04; C12Q 1/68
[52] U.S. Cl. .................... 435/172.3; 435/69.1; 435/69.8; 435/317.1; 435/320.1; 435/6; 530/395; 536/27; 935/6; 935/21; 935/30; 935/48; 935/64; 935/80
[58] Field of Search .............. 435/320, 172.3, 317.1; 935/30, 64, 6; 536/27

[56] References Cited

PUBLICATIONS

Ebert et al., 1989, Cell 56:255–262.
Bredemeijer, G. M. M. and Blaas, J. (1981), Theor. Appl. Genet. 59:185–190.
Nishio, T. and Hinata, K. (1979), Jap. J. Genet. 54:307–311.
Nishio, T. and Hinata, K. (1982), Genetics 100:641–647.
Ferrari, T. E. et al. (1981) Plant Physiol. 67:270–277.
Nashralla, J. B. et al. (1985) Nature, 318:263–267.
Takayama et al. (1986), Agric. Biol. Chem. 50:1365–1367.
Takayama et al. (1986) Agric. Biol. Chem. 50:1673–1676.
Takayama et al. (1987) Nature 326:102–105.
Anderson et al. (1986) Nature 321:38–44.
van der Donk, J. A. W. M. (1975), Nature 256:674–675.
Cornish et al. (1987) Nature 326:99–102.
Hinata, K. et al. (1982), Genetics 100:649–657.
Clarke, A. E. (1985), "Molecular Basis of Fertilization in Flowering Plants", Abstr., 1st Intl. Congr. Plant Mol. Biol., Savannah, Ga. held 10/29/85.
Cornish, E. (1985), "Control of Fertilization in Flowering Plants: Cloning of the S-gene Which Prevents Self Fertilization in an Ornamental Tobacco, N. Alata", Abstr. 1st Intl. Congr. of Plant Mol. Biol., Savannah, Ga., held 10/31/85.
Nashralla et al., U. S. Patent Application Ser. No. 762,245, filed 8/5/85.

*Primary Examiner*—Charles E. Warren
*Assistant Examiner*—P. R. Rhodes
*Attorney, Agent, or Firm*—Greenlee and Associates

[57] ABSTRACT

DNA sequence of S-genes which encode S-proteins and control the self-incompatibility reaction in gametophytic self-incompatible plants have been identified. The DNA sequence encoding several S-proteins of *N. alata* and their attendant signal sequences are specifically provided. Regulatory sequences which direct expression of the S-genes in reproduction tissue of self-incompatible plants have also been identified. A method for the identification and isolation of cDNA and genomic DNA coding sequences of the S-genes is described.

44 Claims, 7 Drawing Sheets $\underline{S}_2\underline{S}_3$

P=PETAL
L=LEAF
O=OVARY
A=ANTHER
S=STYLE

LANES: 1 2 3     4 5 6

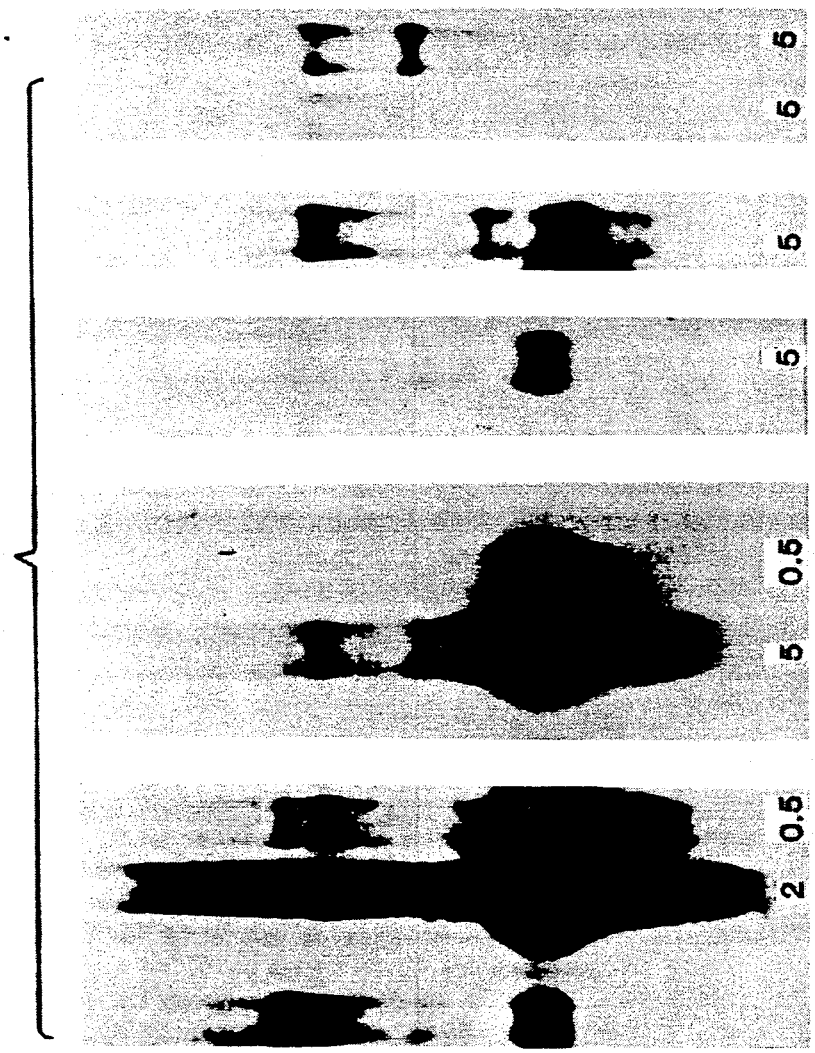

SELF-INCOMPATIBILITY GENE

This is a continuation-in-part of U.S. patent application Ser. No. 854,139, filed Apr. 21, 1986, which in turn is a continuation-in-part of U.S. patent application Ser. No. 792,435, filed Oct. 29, 1985, now abandoned.

FIELD OF THE INVENTION

This invention relates to the identification and isolation of cDNA and genomic DNA coding sequences of an S-gene which controls self-incompatibility in a wide variety of self-incompatible plants, particularly exemplified by members of the Solanaceae. Studies of S-gene products, S-proteins, indicate that they are associated with the expression of the self-incompatibility genotype of such self-incompatible plants.

S-proteins are useful in control of pollen tube growth, for example as natural gametocides to control, induce or promote self-incompatibility and interspecific incompatibility. S-genes and their products can also be used in genetic manipulation of plants to create self-incompatible cultivars. Plants engineered in this way will be valuable for the economic production of hybrid seed.

BACKGROUND OF THE INVENTION

Many plant species, including *Nicotiana alata* and *Lycopersicon peruvianum*, are self-incompatible, that is they cannot be fertilized by pollen from themselves or by that of a plant of the same S- (or self-incompatibility) genotype. The molecular basis of self-incompatibility is believed to arise from the presence of S-protein in the mature styles of plants; in particular, as exemplified by *N alata* and *L. peruvianum*, S-protein has now been shown to be present in extracts of plant styles at the developmental stages of buds at first show of petal color, and at the subsequent stages of maturation of open but immature flowers, and flowers having mature glistening styles. On the other hand, S-protein is not present in the earlier developmental stages of green bud and elongated bud.

For general reviews of self-incompatibility, see de Nettancourt (1977) *Incompatibility in Angiosperms*, Springer-Verlag, Berlin; Heslop-Harrison (1978) Proc. Roy. Soc. London B, 202:73; Lewis (1979) N. Z. J. Bot. 17:637; Pandey (1979) N.Z. J. Bot. 17:645 and Mulcahy (1983) Science 220:1247. Self-incompatibility is defined as the inability of female hermaphrodite seed plants to produce zygotes after self-pollination. Two types of self-incompatibility, gametophytic and sporophytic, are recognized. Gametophytic incompatibility is most common and in many cases is controlled by a single nuclear gene locus (S-locus) with multiple alleles. Pollen expresses its haploid S-genotype and matings are incompatible if the S-allele expressed is the same as either of the S-alleles expressed in the diploid tissue of the pistil. During both incompatible and compatible matings, pollen tubes germinate and grow through the stigma into the transmitting tissue of the style. Tube growth from incompatible pollen grains is arrested in the upper third of the style.

In sporophytic incompatibility, pollen behavior is determined by the genotype of the pollen-producing plant. If either of the two S-alleles in the pollen parent is also present in the style, pollen tube growth is inhibited. Unlike the gametophytic systems, inhibition usually occurs at the stigma surface and not in the style. In sporophytic incompatibility, S-protein may be concentrated at or near the stigma surface. The gametophytic polyallelic system is considered to be the ancestral form of self incompatibility in flowering plants with the sporophytic system being derived from it (de Nettancourt 1977, supra). The products of the S-gene in the two systems are considered to be structurally related.

There are five species of gametophytically self-incompatible plants and two species of sporophytically incompatible plants in which style or stigma proteins apparently related to S-genotype have been detected by either electrophoretic or immunological methods. In alata, an association between specific protein bands and three S-allele groups was demonstrated by isoelectric focussing of stylar extracts (Bredemeijer and Blaas (1981) Theor. Appl. Genet. 59:185). Two major antigenic components have been identified in mature styles of a *Prunus avium* cultivar of $S_3S_4$ genotype, one of which (S-antigen) was specific to the particular S-allele group (Raff, et al. (1981) Planta 153:125; and Mau, et al. (1982) Planta 156:505). The S-antigen, a glycoprotein, was a potent inhibitor of the in vitro growth of pollen tubes from a $S_3S_4$ cultivar (Williams et al. (1982) Planta 156:577). The glycoprotein was resolved into two components, purportedly representing the $S_3$ and $S_4$ products of the $S_3S_4$ genotype. Stylar protein components which have been associated with the S-allele group or the self-incompatibility genotype are reported in *Petunia hybrida* (Linskens (1960) Z. Bot. 48:126), *Lilium longiflorum* and *Trifolium pratens* (Heslop-Harrison (1982) Ann. Bot. 49:729).

A glycoprotein corresponding to genotype $S_7$ of *Brassica campestris* has been isolated from extracts of stigmas by gel-filtration followed by affinity chromatography and isoelectric focussing (Nishio and Hinata (1979) Jap. J. Genet. 54:307). Similar techniques were used to isolate S-specific glycoproteins from stigma extracts of *Brassica oleracea* plants homozygous for S-alleles $S_{39}$, $S_{22}$ and $S_7$ (Nishio and Hinata (1982) Genetics 100:641). Antisera raised to each isolated S-specific *Brassica oleracea* glycoprotein not only precipitated its homologous glycoprotein but also reacted with the other two S-specific glycoproteins of *B. oleracea* and the $S_7$-specific glycoprotein of *B. campestris* (Hinata et al. (1982) Genetics 100:649). An S-specific glycoprotein was isolated by Ferrari et al. (1981) Plant Physiol. 67:270 from a stigma extract of *B. oleracea* using sucrose gradient sedimentation and double diffusion tests in gels in which the proteins were identified by Coomassie Blue staining. This preparation was shown to be biologically active since pretreatment of $S_2S_2$ pollen with the glycoprotein prevented the pollen from germinating on normally compatible stigmas. Recently a cDNA clone encoding part of an S-locus specific glycoprotein from *B. oleracea* stigmas has been described (Nasrallah et al. (1985) Nature 318:263-267.

In work that is detailed in Clarke et al., U.S. patent applications Ser. No. 615,079, filed May 24, 1984, and Ser. No. 050,747, filed May 15, 1987, stylar extracts of several self-incompatibility genotypes from both *Nicotiana alata* and *Lycopersicon peruvianum* were examined for the presence of S-gene associated protein. Glycoprotein materials were identified in the 30,000 MW region of stylar extracts of genotypes $S_1S_3$, $S_2S_3$, $S_2S_2$ and $S_3S_3$ of *N. alata* and of genotypes $S_1S_2$, $S_2S_3$, $S_1S_3$, $S_2S_2$, $S_3S_3$ and $S_3S_4$ of *L. peruvianum*. By comparing two-dimensional gel electrophoresis of stylar extracts of the different genotypes, closely related, but distinct glycoproteins were found to segregate with the individual S-alleles. For example, the *N. alata* S$_2$-protein was found only in stylar extracts of the genotypes containing the S$_2$-alleles (S$_2$S$_3$ and S$_2$S$_2$). For each genotype, the genotype specific glycoprotein only appeared as the flower matured, and was detected only in stylar extracts of buds at first show of petal color and in later stages of maturation, but not in earlier bud stages. Therefore, the appearance of these glycoproteins is temporally coincident with the appearance of the self-incompatibility phenotype. The S$_2$-glycoprotein of *N. alata* and the S$_2$ and S$_3$-proteins of *L. peruvianum* were shown to be more highly concentrated in the upper style sections, which is the zone in which pollen tube inhibition occurs. Therefore, the appearance of these glycoproteins is spatially coincident with the self-incompatibility reaction. Further, corroboration of the biological activity of S$_2$-protein of *N. alata* was demonstrated by its inhibition of pollen tube growth in an in vitro assay (Williams, et al., 1982, supra).

A significant aspect of the work disclosed in U.S. application Ser. Nos. 615,079 and 050,747 was the discovery that rabbit antisera and monoclonal antibodies raised to individual S-proteins or stylar extracts showed immunological cross-reaction between S-proteins of different genotype within the same species, between S-proteins of different species and also between species having gametophytic incompatibility and sporophytic incompatibility. It was concluded therein that there is structural homology among S-proteins, and that despite apparent differences in molecular weight and pI, these proteins are a recognizable structural class in addition to their functional similarities.

These applications also reported the results of N-ter-,oma; sequencing of several mature *N. a;ata* (S$_2$, S$_6$, S$_Z$ and S$_{f1}$) proteins and *L. peruvianum* (S$_1$ and S$_3$) proteins. Significant amino acid sequence homologies among these gametophytic S-proteins were found. In the region sequenced (amino acids 1-15), the *N. alata* S$_2$ protein is 80% homologous to the *N. alata* S$_6$ protein, 67% homologous to the *L. peruvianum* S$_1$ protein, 53% homologous to the *L. peruvianum* S$_3$ protein.

U.S. application Ser. Nos. 615,079 and 050,747 also disclosed a method of purification for S-proteins which included fractionation of stylar extracts by ion exchange chromatography followed by a second fractionation by affinity chromatography. The method of purification was exemplified with the isolation of the 32K S$_2$-glycoprotein from *Nicotiana alata* styles.

Recent reports of the isolation and amino acid sequence of the S$_8$, S$_9$ and S$_{12}$ proteins of *Brassica campestris* show that there is extensive homology among these gametophytic S-proteins (Takayama et al. (1986) Agric. Biol. Chem. 50:136501367; Takayama et al. (1986) ibid. p. 1673-1676; Takayama et al. (1987) Nature 326:102-105). The predicted amino acid sequence of the S$_6$ protein of *B. oleracea* (Takayama et al., 1987, supra) based on the DNA sequence of an S$_6$ gene cDNA clone (Nasrallah et al., 1985, supra) is found to be about 75% homologous to the *B. campestris* S-proteins. Comparison of the *N. alata* and *L. peruvianum* S-protein sequences (U.S. patent applications Ser. No. 615,079 and 050,747; Anderson et al. (1986) Nature 321:38-44) with those of the Brassica S-proteins indicate that there is no significant homology between the gametophytic and sporophytic S-proteins.

The S-proteins that have been identified are glycoproteins, which are proteins that have been modified by covalent bonding of one or more carbohydrate groups.

Little is known of the composition and structure of the carbohydrate portion of S-proteins. It is, as yet, unclear what contribution, if any, the carbohydrate portion of the S-protein makes to biological activity in the incompatibility reaction. *Petunia hybrida* stylar mRNA is translated in *Xenopus laevis* (frog) egg cells to produce active proteins which induce the incompatibility reaction. The relative glycosylation of S-proteins produced in frog egg cells to that of the S-proteins produced in the plant is unknown; however, the post-translational processing in the foreign system is adequate to produce biologically active proteins (Donk, van der J. A. W. M., (1975) Nature 256:674-675).

Most proteins, such as the S-proteins, that are excreted from or transported within cells have signal or transit sequences that function in the translocation of the protein, for example see: Perlman, D. and Halverson, H. W., (1983) J. Mol. Biol. 167:391-409; Edens, L. et al. (1984) Cell 37:629-633.; and Messing, J. et al. in *Genetic Engineering of Plants*, ed. Kosuge, T. et al. (1983) Plenum Press, New York, pp. 211-227. Signal or transit DNA sequences are generally adjacent to the 5' end of the DNA encoding the mature protein, are co-transcribed with the mature protein DNA sequence into mRNA and are co-translated to give immature proteins with the signal or transit peptide attached. During the translocation process the signal or transit peptide is cleaved to produce the mature protein.

The expression of S-genes in self-incompatible plants shows very complex regulation, with S-gene products appearing in only certain tissues at certain times. The mechanism of this regulation is not yet known in detail, but involves the presence of specific regulatory DNA sequences in close proximity to the genomic DNA that encodes the S-protein. Adjacent to the structural gene and signal or transit sequences, are promoter sequences that control the initiation of transcription and exert control over protein expression levels.

SUMMARY OF THE INVENTION

It is a goal of the present invention to isolate and characterize the S-genes of gametophytic self-incompatible plants. Toward this goal, methods for isolating cDNA clones of S-genes have been described and have been exemplified by their application to the isolation of near full-length and full-length cDNA clones of the S-genes of plants of the genus Nicotiana, specifically to the isolation of cDNA clones of the S$_2$, S$_3$ and S$_6$ genes of *N. alata*. The methods described are generally applicable to the isolation of cDNA clones of gametophytic self-incompatible plants, including plants which are members of the Solanaceae which includes among others the general Nicotiana and Lycopersicon.

The S-gene cDNA clones of the present invention are useful as probes for the identification of genomic S-gene sequences which include regulatory sequences which direct expression of the S-gene products in plant reproductive tissue including female secretory tissues and pollen. Such methods have been exemplified by their application to the isolation of the genomic sequences of the S$_2$ gene of *N. alata*. Such method are generally applicable to the isolation of genomic sequences of S-genes of gametophytic self-incompatible plants. Full-length S-gene cDNA clones which can be isolated by the methods described herein contain DNA sequences which encode the S-gene protein including its complete signal or transit sequence. This signal sequence functions in the extra cellular translocation of the mature S-protein from the transmitting tract cells. The transmitting tract is the tissue through which the pollen tubes grow on their way to the ovary.

The S-protein DNA coding sequences can be employed, for example, in heterologous in vivo expression systems to direct synthesis of S-protein which can thereby be produced in significant amounts in biologically active form to be used, for example, as natural gametocides. The DNA sequence encoding the mature S-protein can be so employed separately or in combination with its attendant signal and/or regulatory sequences.

Signal or transit sequences are useful in combination with adjacent DNA sequences of the mature protein in affecting the excretion or translocation of mature protein in heterologous expression systems. Signal or transit sequence may also enhance protein expression levels. Signal or transit sequences are useful in the construction of chimaeric genes in which they are fused to a heterologous protein coding sequence, for example in a recombinant vector, to direct translocation of that protein. Plant signal or transit sequences are particularly important for use in combination with their DNA sequences or in chimaeric gene fusions with heterologous coding sequences to target mature protein to specific organelles in plant cells or for excretion from cells.

Near full-length cDNA clones can be employed to isolate full-length cDNA clones containing complete coding and signal sequences.

S-gene regulatory sequences isolated as described herein are useful in combination with DNA sequences encoding protein (i.e., structural genes) in effecting transcription of the DNA coding sequences and exerting control over protein expression levels in heterologous expression systems. In particular, S-gene regulatory sequences are useful for the expression of heterologous protein in reproductive tissue of plants. For example, the S-gene regulatory sequences can be employed in the expression of toxic proteins in plant reproductive tissue, particularly in pollen tissue. The specifically expressed toxin would function as a natural gametocide.

The present invention provides novel genetic constructs (recombinant DNA molecules and vectors) containing DNA sequence encoding S-proteins of gametophytic self-incompatible plants. Constructs containing S-gene signal sequences and S-gene regulatory sequences alone or in combination with S-gene coding sequences or heterologous coding sequences are also described.

S-gene regulatory sequences, as exemplified by the $S_2$ gene of *Nicotiana alata* have been found to contain regions highly homologous to mitochondrial DNA. The high conservation of these regions and their positioning in the 5'-flanking region of the S-gene indicate that they function in the tissue specific regulation of the S-gene.

In a particular aspect of the present invention, a novel method for the identification and isolation of S-gene cDNA of a gametophytic self-incompatible plant has been provided. This method involves the steps of preparing a cDNA library from an appropriate S-genotype of the self-incompatible plant (i.e., of an S-genotype which expresses the S-gene to be isolated) and subjecting the cDNA library to differential hybridization screening. The cDNA library is screened with a first cDNA probe prepared from mature style RNA of plants of an S-genotype which expresses the S-gene to be cloned and a second cDNA probe prepared from mature style RNA of plants of an S-genotype which is different from the S-genotype used to prepare the cDNA library and which does not express the S-gene to be cloned. Clones which hybridize more strongly to the first probe than to the second probe are selected. The selected clones are then employed as probes in northern blot hybridizations of style RNA from several S-genotypes. Clones that hybridize more strongly to RNA preparations from S-genotypes which express the target S-gene than to RNA preparations from S-genotypes which do not express the target S-gene are selected as cDNA clones of the target S-gene. Any such cDNA clones which are not full-length clones can be employed in conventional hybridization screening of the cDNA library to isolate full-length clones.

It is preferred in this method that the cDNA library and the cDNA probes employed in differential screening be prepared from mature style RNA of homozygous S-genotypes. In such a case, the first cDNA probe is prepared from styles of the same homozygous S-genotype as the cDNA library, and the second cDNA probe is prepared from styles of a different homozygous S-genotype. It will be readily apparent that heterozygous S-genotypes can also be employed in this method. If probes from heterozygous S-genotypes are employed to screen a homozygous S-genotype cDNA library, then the S-genotype of the first probe must express the target S-gene and the S-genotype of the second probe must not express the target S-gene.

If a heterozygous S-genotype is employed to prepare the cDNA library and homozygous S-genotypes are employed to prepare probes, then the S-genotype of the second cDNA probe must not express either of the S-genes expressed by the styles employed to prepare the cDNA library. Further, if heterozygous S-genotype cDNA probes are employed to screen a heterozygous S-genotype library, the S-genotype of the first probe must express the target S-gene while the S-genotype of the second probe must not express the target S-gene, and in addition, either both of the S-genotypes used to prepare probes must express the non-target S-gene of the cDNA library S-genotype, or neither of the cDNA probe S-genotypes must express the non-target S-gene of the cDNA library S-genotype

BRIEF DESCRIPTION OF THE FIGURES

FIG. 1 illustrates the separation of stylar extracts of *N. alata* genotypes $S_2S_2$, $S_2S_3$ and $S_3S_3$ by selected 2-dimensional gel electrophoresis. The protein bands associated with the two alleles are identified.

FIG. 2 provides a comparison of (A) the chemically deglycosylated mature $S_2$ glycoprotein of *N. alata* of mollecular weight 26 kd, with the (B) in vitro translation products of style poly(A+) RNA, by SDS-gel electrophoresis. Note the presence of the 27 kd molecular weight protein band only in the translation products from mature style poly(A+) RNA. The 27 kd molecular weight translation product (lane 1) is slightly larger than the chemically deglycosylated mature $S_2$ protein (lane 2), consistent with the presence of a signal sequence in the 27 kd protein.

FIG. 3 presents a comparison of the SDS-polyacrylamide gel electrophoresis of protein extracts from ovary, style and other *N. alata* ($S_2S_3$) tissue. There is more similarity between the extracts of ovary and style than between extracts of other organs and style, as shown by the protein bands visualized by Coomassie Blue staining.

FIG. 4 shows the production of a 10 bp cDNA fragment from mature style poly(A+) RNA using synthetic oligonucleotide 14-mers as primers. One batch primed synthesis of a single 100 bp fragment (tracks 1, 2 and 3). Tracks 4, 5, and 6 show that only the 100 bp fragment is produced with mature style poly (A+) RNA when pooled synthetic primers are used. Only traces of the 100 bp fragment are detected from ovary and green bud style poly(A+) RNA.

FIG. 5 is a Northern blot analysis of mature style poly(A+) RNA from $N.$ alata genotypes $S_3S_3$, $S_1S_3$, $S_2S_2$ and $S_2S_3$. $L.$ peruvianum genotypes SlS$_3$ and mixed genotypes from $B.$ oleracea. Poly(A+) RNA from $N.$ alata $S_2S_3$ green bud style and ovary are also included. All tracks are probed with $^{32}$P-labelled probe from the NA-2-1 clone cDNA insert encoding the $N.$ alata $S_2$-protein described infra.

FIG. 6 contains autoradiograms of Southern hybridization blots of $N.$ alata (N.a.) and $L.$ esculentum (L.e.) total and mitochondrial DNA (mtDNA) digested with HindIII in which the hybridization probe was (FIG. 6A) the 1.0 kb genomic $S_2$ gene fragment or (FIG. 6B) the 750 bp mitochondrial clone from $N.$ alata. Samples of total DNA contain 5 μg and the mtDNA samples contain approximately 200 ng. Lane 5 of panel A contains an undigested sample of $L.$ esculentum mtDNA. Molecular weight references in kilobase pairs are indicated.

FIG. 7 contains autoradiograms of Southern hybridization blots of total DNA probed with the 750 bp mitochondrial clone. FIG. 7A is a long exposure autoradiogram of a blot containing total DNA of $N.$ alata (N.a.), $L.$ esculentum (L.e.) and $L.$ pennellii (L.p.). A total of 5 μg of DNA digested with HindIII was employed in each lane. Variation in the signal of the strongly hybridizing 750 bp band in this blot is due to different amounts of mtDNA contamination in the total DNA samples. Molecular weight markers are indicated. FIG. 7B is a blot containing total DNA (5 μg samples, digested with EcoRI) from six F2 progeny from a cross between $L.$ esculentum and $L.$ pennellii. Arrows indicate segregating fragments.

DETAILED DESCRIPTION OF THE INVENTION

Figure 2:
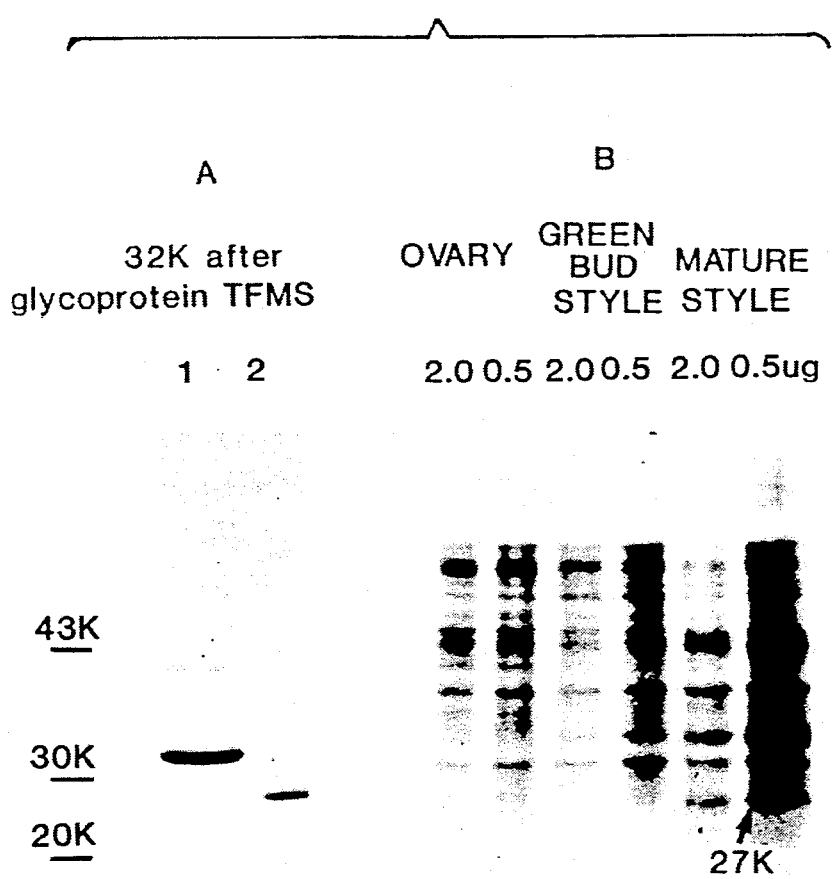

The following definitions apply in the specification and claims:

The S-gene protein is the product of the S-gene or S-allele. The term protein as used herein also includes glycoprotein. Although the biochemical mechanism of the self-incompatibility reaction is not fully understood, the S-protein is associated with the presence of self-incompatibility. Accordingly, the S-protein must (1) show segregation with the S-allele; (2) be localized in the tissue where the incompatibility reaction is localized and (3) occur in the appropriate plant tissue in coincidence with the expression of self-incompatibility. In addition, it will be understood that the biological activity of the S-protein in an in vitro assay will provide corroboration that the S-protein is itself functionally active for pollen inhibition. However, it is possible that the active component is a modified protein or a secondary product. In such cases, biological activity of the S-protein may require the activity of other components in order to be manifested in a bio-assay system. A mature S-protein is the processed form of the S-protein from which the signal or transit peptide has been cleaved. This is the form of the protein isolated from stylar tissue.

The S-gene or S-allele contains the DNA coding sequences for the mature S-proteins defined above. Further, the S-gene contains the coding region for a signal or transit peptide and other information necessary to the translation and processing of the S-protein. Further, the S-gene contains regulatory and promoter sequences involved in the transcription and expression and processing of the S-protein. Plant genomic sequences may contain introns. A full length cDNA clone comprises the DNA sequence encoding a mature protein and the entire signal or transit sequence.

A self-incompatible plant may have heterozygous S-genotype in which two different S-alleles are expressed (i.e., $S_1S_3$) or have a homozygous S-genotype in which the two alleles are the same (i.e., $S_1S_1$).

The term regulatory sequence is used herein to refer to the DNA sequences associated with an S-gene which functions to regulate tissue specific expression of S protein (the S-gene product) in plant reproductive tissue. Plant reproductive tissue includes female secretory tissue (the stigma, style transmitting tissue and the epidermis of the placenta) and pollen. Sequences which function for regulation of expression of structural genes are most often present in the 5'-flanking region of the gene extending up to about 1 to 2 kb upstream from the transcription start site. The 5'-regulatory sequence includes a region which is termed the promoter which functions specifically for the initiation of transcription. Promoter sequences are necessary, but not always sufficient, to drive the expression of a downstream gene. Eukaryotic promoters generally contain a sequence with homology to the consensus 5'-TATAAT-3' ("TATA" box) about 10–35 bp 5' to the transcription start site. About 30–70 bp 5' to the "TATA" box there is often another promoter component with homology to the canonical form 5'-CCAAT-3', which in plants is sometimes replaced by a "AGGA" box which is a region having adenine residues symmetrically flanking the base triplet "G(or T)NG". Sequence elements associated with modulation of expression, including expression in response to stimuli, such as anaerobiosis and light and tissue specific expression are often found further upstream of the promoter region but can be found interspersed with the promoter elements. The sequences which function to modulate when and where a gene is expressed can comprise one or more sequence elements separated by non-functional sequence. In such cases, the distance separating the functional sequence elements can also be important for correct regulation. Certain sequence elements can function as on/off switches, for example inducing expression in certain tissue and little or no expression in other tissue. Such sequence elements can function in concert with other sequence elements which modulate the level of expression.

Placing a structural gene under the regulatory control of a promoter or a regulatory sequence means positioning the structural gene such that the expression of the gene is controlled by these sequences. Promoters and regulatory sequence elements are generally positioned upstream of the genes that they control. In the construction of a chimaeric gene in which a heterologous structural gene is placed under the control of a regulatory sequence, it is generally preferred to position the regulatory sequence at a distance from the gene transcription start site that is approximately the same as the distance between that sequence and the homologous gene that it controls in its natural setting, i.e., the gene from which the regulatory sequence is derived. As is known in the art, some variation in this distance can be accommodated without loss of regulatory control and, in fact, certain variations can lead to improved control or higher expression levels.

A structural gene is that portion of a gene comprising a DNA segment encoding a protein, polypeptide or a portion thereof. Structural genes may include signal or transit sequences, and may refer to a gene naturally found within a plant cell but artificially introduced, particularly as part of a chimaeric construct in which it is placed under the control of the tissue-specific regulatory sequences of the present invention. The structural gene may be derived in whole or in part from a bacterial genome or episome, eukaryotic genomic or plastid DNA, cDNA, viral DNA, or chemically synthesized DNA. Such a structural gene may contain modifications (including mutations, insertions, deletions and substitutions) in the coding or the untranslated regions which could affect biological activity or the chemical structure of the expression product, the rate of expression or the manner of expression control. The structural gene may constitute an uninterrupted coding sequence, or it may include one or more introns. The structural gene can encode fusion protein so long as functionality is maintained in the joining of coding sequences. The structural gene can be a composite of segments derived from a plurality of sources. The structural gene can be a composite comprising signal or transit sequence from one gene and a sequence encoding a mature protein from another gene. For example, the structural gene can be a composite having the signal or transit sequence of an S gene and the coding region of another gene.

The term cDNA is understood in the art to denote the single stranded complementary DNA copy made by action of reverse transcriptase on an mRNA template. Herein, the term cDNA is also used to denote any single or double stranded DNA that is replicated from this first complementary copy. cDNA coding sequences are distinguished from genomic DNA sequences by the potential presence of intron non-coding sequences in the genomic DNA. In vivo, introns are removed from messenger RNA by splicing events that produce mature mRNA. It is mature mRNA that is used in the initial preparation of cDNA by reverse transcription.

The term recombinant DNA molecule is used herein to distinguish DNA molecules in which heterologous DNA sequences have been artificially ligated together by the techniques of genetic engineering, for example by in vitro ligation using DNA ligase (Maniatis, T. et al. (1982) *Molecular Clonging*, Cold Spring Harbor Laboratory, Cold Spring Harbor, N.Y.). Heterologous DNA sequences are derived from different genetic entities.

The process of cloning a DNA fragment involves excision and isolation of the DNA fragment from its natural source, insertion of the DNA fragment into a recombinant vector and incorporation of the vector into a microorganism or cell where the vector and inserted DNA fragment are replicated during proliferation of the microorganism or cell. The term clone is used to designate an exact copy of a particular DNA fragment. The term is also used to designate both the microorganism or cell into which heterologous DNA fragments are initially inserted and the line of genetically identical organisms or cells that are derived therefrom.

The term recombinant vector is used herein to designate a DNA molecule capable of autonomous replication in a host eukaryotic or prokaryotic cell, into which heterologous DNA sequences can be inserted, so that the heterologous sequences are replicated in the host cell. Conventional techniques known to those of ordinary skill in the art are used to introduce the vector into its host cell (Maniatis et al., 1982, supra). Recombinant vectors often contain a marker displaying a selectable phenotype such as antibiotic resistance to allow selection of transformed cells.

A DNA molecule that is substantially pure will migrate as a single band in agarose or polyacrylamide gel electrophoresis, using conventional procedures described in Maniatis et al. (1982), supra, and exemplified in FIGS. 4, 6 and 7.

The term homology is used in the art to describe a degree of amino acid or nucleotide sequence identity between polypeptides or polynucleotides. The presence of sequence homology is often used to support a genetic or functional relationship between polypeptides or nucleotide sequences. The presence of amino acid sequence homology between polypeptides implies homology between the DNA sequences that encode the individual polypeptides. Since the genetic code is degenerate the degree of homology between polypeptides or proteins is not necessarily the same as that between the DNA sequences that encode them. The degree of homology between polypeptides or polynucleotides can be quantitatively determined as a percent homology if the sequences are known. In the absence of sequence information for comparison, the presence of homology is usually determined operationally by experiment. In the case of DNA or RNA sequences, hybridization experiments are used to determine the presence or absence of homology. Since the strength of a particular hybridization signal depends on the experimental conditions used as well as the degree of homology, it is convenient to define homology in relation to the experimental conditions used. We use the term substantially homologous as the degree of homology that must exist between the hybridization probe and a target RNA or DNA sequence in order to select the target sequence from a background of undesired sequences using hybridization experiments as described herein.

Except as noted hereafter, standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in: Maniatis et al. (1982), supra; Wu (ed.) (1979) Meth. Enzymol. 68; Wu et al. (eds.) (1983) Meth. Enzymol. 100 and 101; Grossman and Moldave (1980) (eds.) Meth. Enzymol. 65: Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Sellow and Hollaender (1979) *Genetic Engineering: Principles and Methods*, Vols. 1-4, Plenum Press, New York. Abbreviations and nomenclature, where employed, are deemed standard in the field and commonly used in professional journals such as those cited herein.

The present work describes the isolation and identification of cDNA and genomic DNA encoding S-gene proteins of gametophytic self-incompatible plants, particularly those encoding the S-genes of *Nicotiana alata*. The initial isolation of cDNA of S-genes, as applied to the $S_2$-gene of *Nicotiana alata*, involved the preparation of a cDNA library from poly(A+) RNA of mature styles which was then differentially screened employing radioactively labelled cDNA from ovary and green bud style to remove non-mature style specific cDNA. The resulting mature style specific clones were then probed with an oligonucleotide probe specific for the desired S-gene. The specific probe was based on either the amino acid sequence of the S-protein or on the nucleotide sequence of a cDNA fragment produced from stylar mRNA by specific priming with mixed oligonucleotide primers which was based on the amino acid sequence of the S-protein. Alternatively, the specifically primed cDNA fragment can be used directly as a probe of the mature style clones. Screening of the mature style clones with an S-gene specific probe results in the isolation of cDNA clones which contain S-gene coding sequences including those which are full length and encode the entire S-protein and its attendant signal or transit sequence. In general, the procedure described above is applicable to the isolation of any gametophytic S-gene cDNA.

The alternative methods for screening the mature style specific clone library to obtain S-gene cDNA require a knowledge of the amino acid sequence of the S-protein. S-protein is made in minuscule amounts at limited times in limited tissue. Several hundred styles must be dissected from flowers in order to obtain sufficient pure S-protein for micro-amino acid sequencing. Consequently, the determination of S-protein amino acid sequence requires significant time and effort. Alternative screening methods for isolating S-gene cDNA clones are therefore desirable. Initially it was believed that there was enough structural similarity between the S-gene coding regions, as indicted by hybridization experiments and N-terminal amino acid sequencing, that the cDNA clone of one S-gene could be employed directly as a probe to isolate cDNA clones of other S-genes. This was expected to be true particularly for S-alleles of the same or related plants. In practice it was found that this direct screening method did not work in all cases. For example, screening of an *Nicotiana alata* $S_3S_3$ cDNA library with the *N. alata* $S_2$ cDNA clone resulted in the isolation of $S_3$ cDNA clones. In contrast, this method was not successful for the isolation of *N. alata* $S_6$ or $S_1$ cDNA clones.

A new screening procedure was developed for the isolation of the various S-alleles of *Nicotiana alata*. This procedure involves the differential screening of a mature style cDNA library with cDNA prepared from styles of the same genotype as the library and cDNA prepared from style RNA of another genotype. This procedure is particularly effective because RNA encoding the S-glycoproteins is very abundant. The S-clones hybridize very strongly to cDNA prepared from RNA of the same genotype, while they hybridize weakly with cDNA from other genotypes. This procedure was specifically employed to isolate *N. alata* $S_3$ and $S_6$-cDNA clones and is generally applicable to the isolation of any *N. alata* S-gene cDNA. Further, the procedure is applicable to the isolation of S-gene cDNA clones in other gametophytic species if the variation in DNA sequence among the S-alleles in that species is comparable to the DNA sequence differences among *Nicotiana alata* S-alleles. This procedure is not expected to work for selecting S-alleles in the sporophytic system since there appears to be much higher homology (70-75%) among the various S-alleles of Brassica.

Once S-gene cDNA clones are isolated they can be employed as hybridization probes of genomic DNA to locate and isolate genomic S-gene clones. This procedure has been used specifically to isolate the $S_2$-gene of *Nicotiana alata*, including the $S_2$-protein coding sequence and the 5' and 3' flanking regions of the gene. Within the upstream flanking region of the $S_2$ gene a region having strong homology to mitochondrial DNA of gametophytic self-incompatible plants was identified. This region functions in the regulation of tissue specific expression of the S gene.

Isolation of cDNA encoding the 32 Kd $S_2$-gene protein of *N. alata*

Figure 1:
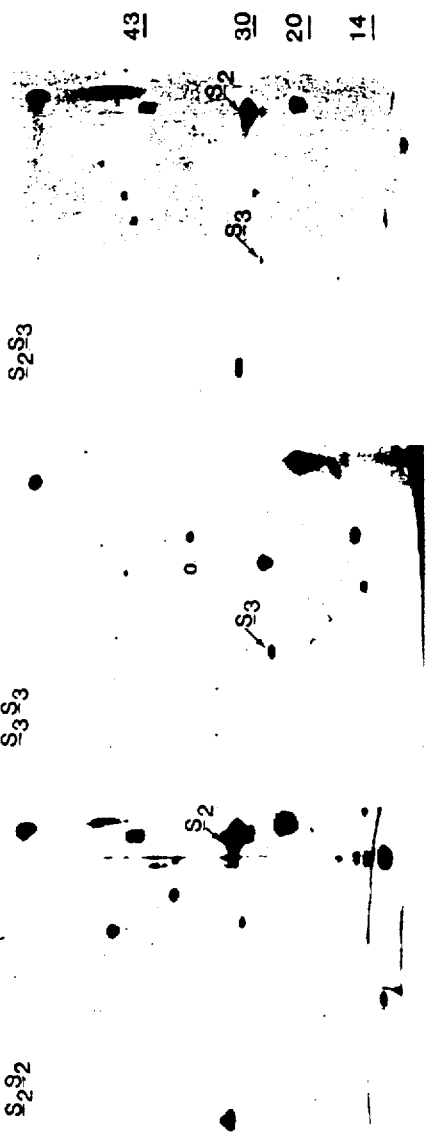

A method for isolating and purifying the S-gene associated glycoproteins from mature styles had been established using a combination of ion exchange and affinity chromatography (U.S. patent application Ser. Nos. 615,079 and 050,747). This method had been applied to the isolation and purification of *N. alata* $S_2$-protein. More recently, purified protein yield improvements have been obtained by using a less basic buffer (pH 7.0 rather than pH 7.8) in affinity chromatography. The S-protein appears to be more stable at lower pH. As illustrated in FIG. 1, it was possible to isolate a single component of MW 32 Kd associated with the $S_2$-allele of *Nicotiana alata*. Chemical deglycosylation of this component yielded a single product of approximately 26 kd in molecular weight, shown in FIG. 2a. The results of in vitro translation of mRNA from mature styles, green bud style and ovary are shown in FIG. 2b. RNA was isolated by conventional methods. Since most mRNA is polyadenylated, poly(dT) cellulose chromatography was used to isolate mRNA, as poly(A+) RNA. The various poly(A+) RNA fractions were translated using an amino acid depleted rabbit reticulocyte lysate kit (Amersham No. N.150, Arlington Heights, Ill.) in the presence of tritiated amino acids. An in vitro translation product of approximately 27 kd molecular weight was detected only from mature style mRNA. This product was slightly larger than the chemically deglycosylated protein. It was therefore identified as the full length immature $S_2$-protein, which is composed of mature $S_2$-protein and its signal peptide.

Figure 3:
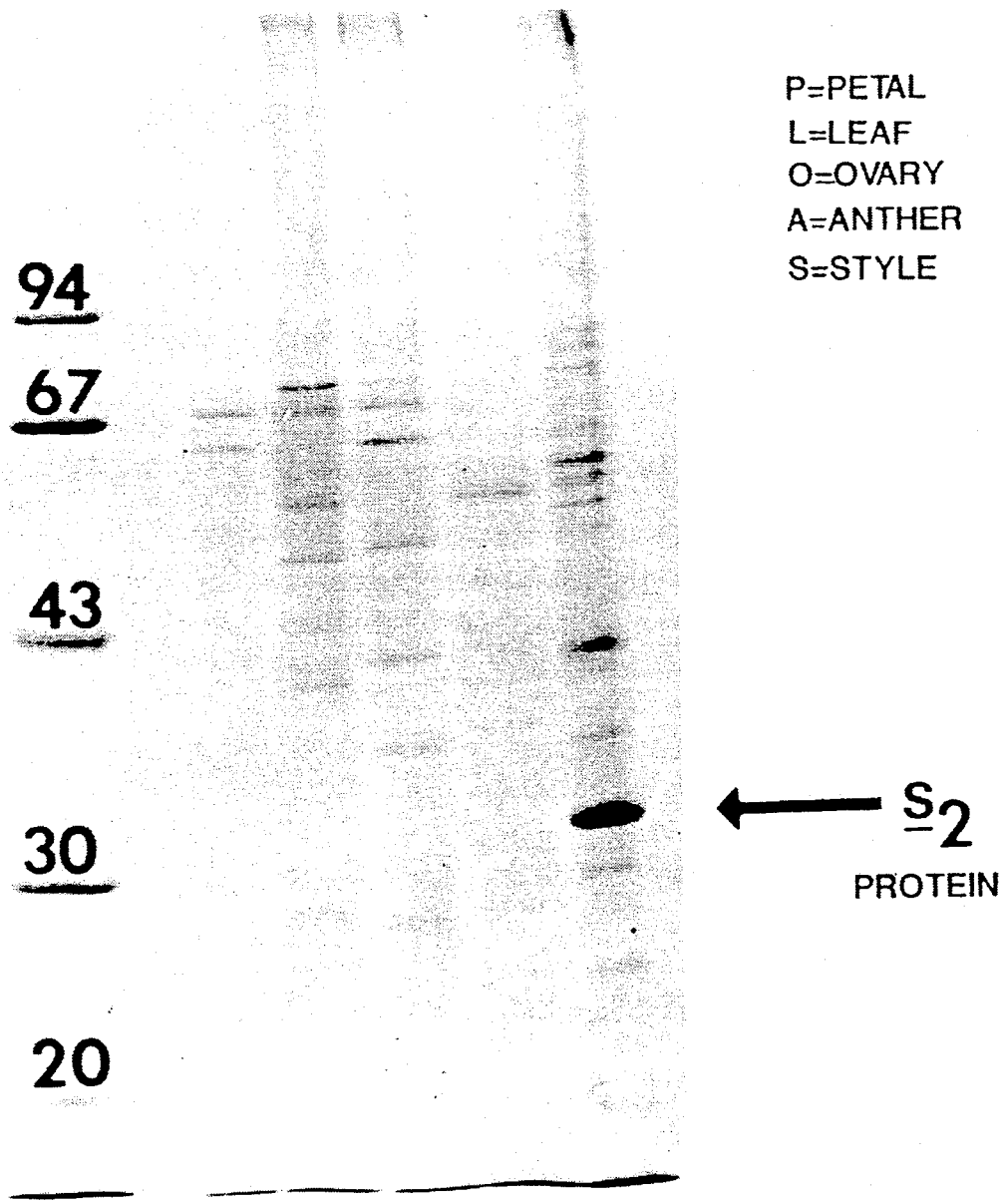

Based on this finding, a protocol of differential screening was adopted as the initial part of the strategy to isolate cDNA coding for $S_2$-protein. A cDNA library was prepared in λgt10 phage using mature style poly(A+) RNA of *N. alata* genotype $S_2S_3$. Mature style poly(A+) RNA was transcribed into double stranded cDNA by conventional methods (Maniatis et al., 1982; supra). End-repair, EcoRI methylation and EcoRI linker ligation reactions were carried out and the cDNA was cloned into the EcoRI site of the λgt10 vector (Huynh, T. et al., (1985) in *Practical Approaches in Biochemistry*, DNA Cloning Vol. 1 ed. Glover, D. IRL Oxford, pp. 49-78). This library was subjected to differential screening using $^{32}$P-labelled cDNA from mature and green bud styles. The lambda-phage was used to infect *Escherichia coli* C600 cells. Plaques that hybridized strongly only to the mature style cDNA were selected and differentially screened a second time using 32P-labelled cDNA prepared from either mature style or ovary mRNA. Again plaques that hybridized strongly only to the mature style cDNA were selected. Ovary cDNA was used in this second screen because SDS-gel electrophoresis indicated that extracts of mature style and ovary had some common proteins which were not expressed in green bud styles (FIG. 3). Surprisingly, tissues other than ovary and green bud were found to be unsuitable sources of cDNA for differential screening since the protein profiles of other organs were found to be too diverse from that of mature style to be useful. Therefore, differential screening with ovary and green bud cDNA, although considerably less convenient, was necessary to discriminate mature style-specific cDNA. The resultant cDNA clones were specific for mature style.

Once the cDNA mature style library had been differentially screened, a $S_2$-protein specific DNA probe was required for final screening of the clone library. The first step in the preparation of the probe was the determination of the N-terminal amino acid sequence of the *N. alata* $S_2$-protein (Table 1). Conventional microsequencing techniques were used (Hewick, R. M. et al. (1981) J. Biol. Chem 256:7990–7997). As a consequence of the limited availability of S-protein, only short segments of N-terminal sequence could be determined using conventional microsequencing techniques. Unfortunately, the N-terminal amino acid sequence of the $S_2$-protein proved to have highly redundant coding oligonucleotide possibilities. Nevertheless, a partial-length cDNA was isolated by the following procedure. A set of synthetic mixed oligonucleotide primers were prepared based on the partial amino acid sequence. A set of 24 14-mers, covering all the codon ambiguities at amino acids 4–8, was synthesized. These synthetic mixed oligonucleotides were then used in three batches of eight 14-mers each, to prime synthesis of cDNA from *N. alata* ($S_2S_3$) mature style poly(A+) RNA.

Figure 4:

As shown in FIG. 4, only one batch (No. 165) was found to be specific for the priming reaction. Surprisingly, a single cDNA band 100 nucleotides in length was identified in this reaction. A 100 bp-nucleotide band was also observed when the pooled 14-mers were used to prime poly(A+) RNA from mature styles; only traces of this fragment were detected in priming from ovary or green bud style mRNA.

The 100 nucleotide long band was eluted from an acrylamide gel and sequenced yielding the $S_2$-protein coding sequence from amino acid -12 in the signal sequence, up to amino acid 2 of the mature protein, Table 2. From this sequence a single 30-mer was synthesized which covered the part of the signal sequence to −9 and included the first amino acid codon of the coding sequence (Table 2). This amino acid region was chosen in order to insure that the synthetic probe would identify cDNA clones that extended into the signal sequence codons. This strategy was adopted for convenience, since adequately large amounts of the synthetic probe could be prepared in a single synthesis. Alternatively, the 100 bp fragment could have been cloned, amplified, purified and radioactively labelled for use as a probe.

The 30-mer was used as an $S_2$-protein specific probe to screen the mature style-specific clones previously identified by differential screening. One of the clones obtained was chosen for further study. The clone, designated NA-2-1, contained a cDNA insert of 877 bp which could be excised as a single fragment from the lambda vector by EcoRI digestion.

In sequencing the NA-2-1 insert it was found that it did not extend in the 5' direction to an ATG initiation codon, and so did not contain the full signal sequence. A full-length clone was obtained from a second cDNA library which had been prepared using a method (Okayama et al. (1982) Mol. Cell Biol. 2:161-170) which optimizes the recovery of full length clones. This library was screened with the 30-mer probe as well as with the cDNA insert from clone NA-2-1 (described above). A clone designated NA-2-2 was obtained which hybridized to both probes. Table 3 provides the nucleotide sequence of the cDNA insert from NA-2-2.

The sequence of the full length cDNA insert of clone NA-2-2 (Table 3) includes an ATG at its 5' end that is a potential initiation codon. The sequence contains an open reading frame of 642 bp which encodes a protein with a predicted molecular weight of 24,847 that includes a putative signal sequence of 22 amino acids. Table 8 provides the amino acid abbreviations used in the Tables of sequences. The sequence of Table 3 encodes the mature $S_2$-protein (192 amino acids) with a signal sequence that would direct the extracellular transfer of the $S_2$ glycoprotein from the transmitting tract cells. The full-length signal sequence has the typical features described for eukaryotic signal sequences (von Heijne (1983) Eur. J. Biochem 133:17–21; and von Heijne (1985) J. Mol Biol. 184:99–105).

The initially isolated NA-2-1 $S_2$ cDNA clone contained the entire $S_2$-protein coding region, part of the signal sequence, and a poly(A+) tail 18 residues long. Differences in the sequence of the NA-2-1 cDNA clone and that of the full-length clone are indicated in Table 3.

Apart from the differences at the 5' end, clones NA-2-1 and NA-2-2 also differ in the length of their 3' untranslated sequence. They are identical to nucleotide 682, which is the polyadenylation site in clone NA-2-2. The clone insert from NA-2-1 has an additional 50 nucleotides of untranslated mRNA and a polyA tail of 18 residues. This difference at the 3' end suggests that there are alternative polyadenylation sites in $S_2$ RNA transcripts.

It will be obvious to one of ordinary skill in the art that the DNA sequence information provided herein can be used for the chemical synthesis of oligonucleotide probes that can be used in the hybridization screens described herein. See, for example, Caruthers, M. H. (1984) Contemp. Top. Polym. Sci. 5:55–71; Eisenbeis, S. J. et al. (1985) Proc. Natl. Acad. Sci. USA 82:1084–1088.

Hybridization of the *N. alata* $S_2$ protein cDNA clone to poly (A+) RNA from mature styles of *N. alata, L. peruvianum* and *Brassica oleracea*

A $^{32}$P-labelled copy of the cDNA insert from the NA-2-1 clone, which contains the $S_2$-protein coding region, was used in Northern blot hybridization experiments with poly(A+) RNA prepared from mature styles of *N. alata* genotypes $S_1S_3$, $S_2S_3$, $S_2S_2$ and $S_3S_3$, as well as mature styles of *L. peruvianum* genotype $S_1S_3$ and green bud styles and ovaries of *N. alata* genotype $S_2S_3$, FIG. 5. The size of the major transcript in mature styles bearing the $S_2$-allele was 940 bases, based on comparison to 5' end labelled-HindIII-EcoRI markers, with two minor transcripts at 1500 and 3500 bp. The 940 base transcript was also present in RNA from $S_3S_3$ and $S_1S_3$ styles but at a much reduced frequency, that is 1% or less than the level in $S_2S_2$ or $S_2S_3$ styles. The major transcript was not present in green bud RNA but was detected in RNA from ovaries of mature flowers, again at a much lower concentration than that of mature styles (less than 1%).

The $S_1$ and $S_3$ proteins from *L. peruvianum* both have estimated molecular weights of 28 kd. The only hybridization observed with the NA-2-1 clone insert and *L. peruvianum* genotype $S_1S_3$ is to large RNA fragments and is believed to be the result of nonspecific hybridization to ribosomal RNA. Hybridization with *Brassica oleracea* mature style mRNA was faint under the conditions used.

These results indicate homology between the DNA coding sequences of the *N. alata* $S_1$ and $S_3$ proteins and the $S_2$ protein of *N. alata*. Further, they indicate that there is homology between the coding sequences of the *N. alata* $S_2$ protein and those of *Lycopersicon peruvianum* $S_1$ and $S_3$ protein. The origin of the weak hybridization of the $S_2$-protein cDNA probe to poly(A+) RNA from *B. oleracea* is unclear since there is no homology between the cloned S-alleles alleles of *Nicotiana alata* and those of Brassica.

Isolation of cDNA clones of *Nicotiana alata* S-alleles

Although hybridization experiments had initially indicated that the *Nicotiana alata* $S_2$-gene cDNA could be used in direct hybridization screening to obtain cDNA clones of other S-alleles of *N. alata*, this method was found not to be generally successful. Northern analysis had shown that the $S_2$ cDNA clone insert (NA-2-1 or NA-2-2) cross hybridized with $S_3$ mRNA, but the degree of hybridization was about 100 fold lower than that obtained with the $S_2$ cDNA probe on $S_2$ mRNA. While $S_3$ cDNA clones were obtained by direct screening of a mature style specific $S_3S_3$ cDNA library with the $S_2$ probe, they were not strongly hybridizing plaques. Once S-cDNA clones of other *N. alata* S-genes were isolated (see below), it was found that the various S-alleles have only about 55% overall homology at the DNA level. The substantial homology between the *N. alata* S-proteins was confined to the N-terminal region of the protein (Table 1).

A different screening approach based on the structural differences among the *N. alata* S-alleles was then devised to isolate *N. alata* S-allele cDNA, and was applied specifically to the isolation of *N. alata* $S_3$ and $S_6$ cDNA.

A cDNA library was prepared in λgt10 using mRNA from mature styles of genotype $S_3S_3$. Radioactively labelled cDNA was prepared from mature styles of the $S_3S_3$ genotype and the $S_6S_6$ genotype. The cDNA library was then differentially screened employing the labelled cDNA from the different genotypes. Plaques that hybridized strongly to $S_3S_3$ cDNA and weakly to $S_6S_6$ cDNA were selected and rescreened with the $S_2$ cDNA clone. The resulting clones were then used as probes in northern blots containing RNA from several S genotypes. $S_3$ cDNA clones were those that hybridized most strongly to the RNA from styles which carries the $S_3$ allele. Hybridization of the $S_3$ clones to RNA of genotypes which did not carry the $S_3$ allele was significantly weaker (10–100 fold lower). One of the $S_3$ clones was selected for sequencing and its sequence is presented in Table 4. This clone was nearly full length; however, a short subfragment at the 5' end of the clone was inadvertently cleaved when the clone was sequenced. The sequence 5' to the EcoRI site (indicated in Table 4) has been determined by RNA sequencing. The N-terminal amino acid sequence of the mature $S_3$ protein was obtained by microsequencing analysis. The signal sequence has not yet been obtained.

An analogous procedure was employed to isolate $S_6$ cDNA clones from a mature style library of the $S_6S_6$ genotype. Initial selection was made for clones which strongly hybridized to $S_6S_6$ cDNA and weakly hybridized to $S_3S_3$ cDNA. One of the $S_6$ clones was selected for sequencing and its sequence is presented in Table 5. This clone contains the entire $S_6$ protein coding sequence and a portion of the signal sequence. The clone does not extend in the 3' direction to a poly(A) tail.

In general, analogous differential screening procedures can be applied to the isolation of cDNA clones of other S alleles of *Nicotiana alata*.

Isolation of a chromosomal S-gene using an S-allele specific cDNA clone as a hybridization probe DNA can be isolated from a self-incompatible plant of known S genotype by conventional methods, as for example those described by Rivin, C. J. et al. (1982) in *Maize for Biological Research* (W. F. Sheridan, ed.) pp. 161–164, Plant Mol. Biol. Assn. Charlottesville, Va.; and Mazure, B. J. and Chui, C.-F. (1985) Nucl. Acids Res. 13:2373, and Bernatzky and Tanksley (1986) Theor. Appl. Genet. 72:314–321. A genomic DNA library can then be constructed in an appropriate vector. This involves cleaving the genomic DNA with a restriction endonuclease, size selecting DNA fragments and inserting these fragments into a cloning site of the chosen vector. A description of the construction, for example, of a *Nicotiana tabacum* genomic library in the phage lambda has been given by Mazure, B. J. and Chui, C.-F., 1985, supra.

Genomic S-allele clones are selected by screening the genotype specific genomic library with a radioactively labelled cDNA S-allele clone insert hybridization probe, for example in a filter hybridization screen. An appropriate microorganism is infected with the phage lambda containing the genomic library. The infected organisms can be plated on agarose at a concentration of several thousand plaque forming units/plate and replicated onto nitrocellulose filters. The labelled probe can then be applied to the filter and allowed to hybridize. Plaques that show hybridization to the probe are selected, replated and rehybridized until a pure phage is isolated. DNA from selected phage can then be purified, restricted, separated on agarose gels and transferred by blotting to nitrocellulose filters. These filters can then be reprobed with the labelled cDNA S-allele probe to identify those restriction fragments that contain S-protein coding sequences. Standard hybridization conditions for such screens have been described (Maniatis et al., 1982, supra).

This procedure was specifically applied to the isolation of the chromosomal $S_2$ gene of *Nicotiana alata*. Total DNA was isolated from leaves of plants of the $S_2S_2$ genotype. In Southern blot hybridization experiments it was established that labelled $S_2$ cDNA probe (NA-2-1 or NA-2-2) hybridized to a single approximately 3.1 kb fragment generated by EcoRI digestion of $S_2S_2$ genomic DNA. This fragment was cloned into λgt10. The chromosomal $S_2$ gene was then sequenced using the dideoxy method. The sequence of the genomic $S_2$ gene is provided in Table 6. As shown, the $S_2$ coding sequence (nucleotides 1603 2338) is interrupted by a single, 94 bp intron. The transcription start has been mapped, as indicated, to a position 19 bases upstream (at position 1584) of the ATG start codon. The sequence includes 5' regulatory sequences extending 1583 bp upstream of the transcription start and contains sequences required for regulated expression of the $S_2$ gene product in reproductive tissue. A putative "TATA" box is identified at nucleotides 1549–1559. The sequence also includes the two polyadenylation signals identified at the 3' ends of the $S_2$ cDNA clones: $T_1$ (2410–2415) and $T_2$ (2456 - 2461).

Figure 6A:
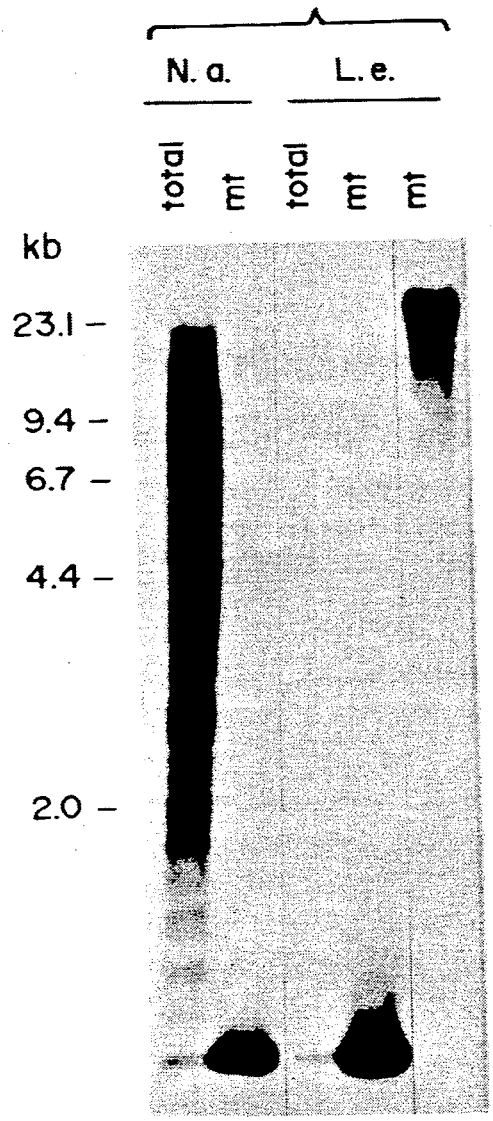
Figure 6B:
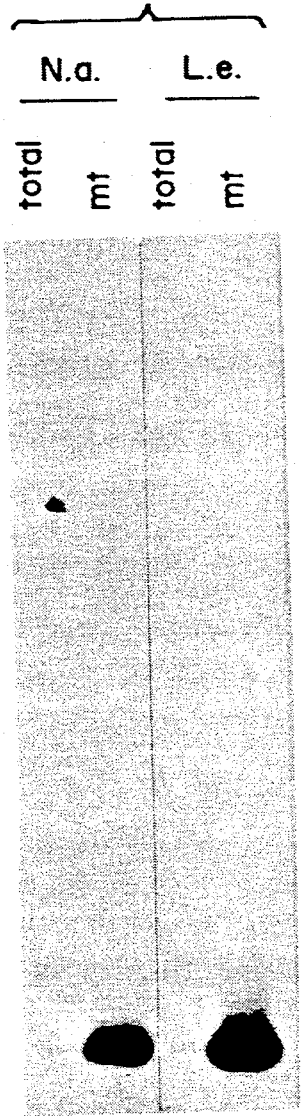

A segment has been identified within the upstream region of the $S_2$ gene that shows homology with mitochondrial DNA on Southern blots. The 3.1 kb $S_2$ gene EcoRI fragment was digested with HincII and an approximately 1 kb fragment which extends from 354 bp upstream of the coding region was isolated and used as a probe in Southern blots of HindIII digests of total DNA from *N. alata* and *Lycopersicon esculentum*. This probe produced a highly repeated pattern including a band of about 750 bp on *N. alata* but only one major band of about 750 bp on *L. esculentum*, FIG. 6A. Subsequent hybridizations with DNA from *L. esculentum* and the related *L. pennellii*, that had been digested with 12 different enzymes revealed no polymorphism of the probe sequence. The 1 kb fragment was also used in Southern blots to probe mitochondrial DNA HindIII digests of *N. alata* and *L. esculentum*, FIG. 6A. The homologous segment is clearly demonstrated in both species to be in the mitochondrial DNA. Further experiments indicated that the homologous sequence is integrated into the high molecular weight chromosomal DNA and not in an extrachromosomal element. The 750 bp mitochondrial DNA fragment of *N. alata* that hybridized to the 1.0 kb HincII fragment was then isolated and used as a probe on Southern blots of HindIII digests of total and mitochondrial DNA of both species (FIG. 6B). The mitochondrial DNA probe hybridized to a single fragment in total and mitochondrial DNA of both species. This indicates that the sequence responsible for the repeated hybridization pattern on total DNA of *N. alata* (FIG. 6A) and the sequence that is homologous to mitochondrial DNA are separate elements on the 1.0 kb subfragment of the $S_2$ gene genomic clone. The 750 bp mitochondrial DNA fragment of *N. alata* was found not to hybridize to mitochondrial DNA of maize under moderate stringency hybridization conditions.

The region of *N. alata* DNA that is homologous to the 1.0 kb $S_2$ gene fragment was found to be confined to a 315 bp HindIII/HincII subfragment of the 750 bp mitochondrial DNA fragment. This subfragment was sequenced and its sequence was compared to that of the upstream region of the $S_2$ gene (Table 7). Alignment of the mitochondrial and nuclear sequence revealed a 56 bp segment of very high homology (53/56 bp). The position of this homologous region in the $S_2$ gene sequence is indicated in Table 6. There are two additional short, perfectly matched sequences 3' from the 56 bp segment (underlined in Tables 6 and 7) which occur in both the mitochondrial and nuclear DNA. The spacing of these two sequences is different in the nuclear and mitochondrial DNA fragments. The nuclear sequence also contains a short 8 bp direct repeat that immediately flanks the region of homology (one of the repeats is within the homologous sequence). The first 7 bp of the repeat perfectly match the terminal portion of the inverted repeat of the S-2 plasmid of maize that is found in the mitochondria of male-sterile cytoplasm (Levings and Sederoff (1983) Proc. Natl. Acad. Sci. USA 80:4055–4059). The presence of direct repeats in the nuclear sequence are consistent with features of transposable element excision (Nevers et al. (1986) Adv. Bot. Res. 12:103–203). The similarities of sequence between the nuclear and mitochondrial DNA segments of Table 7 and the presence of transposable element features suggest that the homologous region has been transferred between organelles, however the direction of transfer is unknown. A comparison of the 56 bp and the entire 315 bp mitochondrial segment with the plant, organelle, viral and structural DNA sequences compiled in the GenBank database (U.S. Department of Health and Human Services, Theoretical Biology and Biophysics Group, Los Alamos Natl. Laboratory, Los Alamos, N.M.) reveals no significant sequence homologies.

Figure 7A:
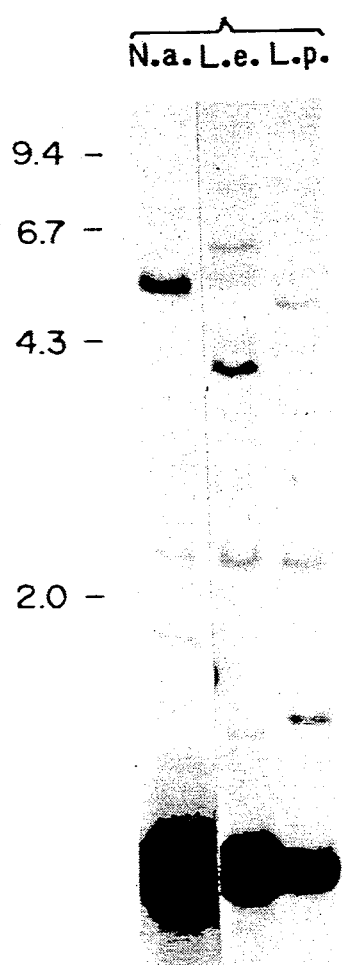
Figure 7B:
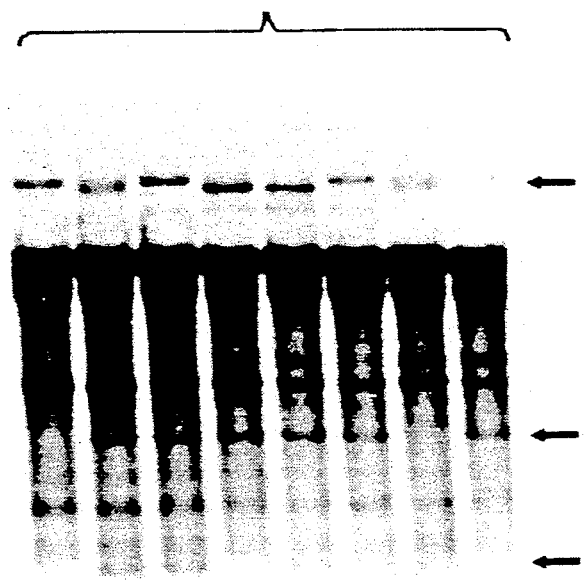

When Southern blots of total DNA digests of *N. alata*, *L. esculentum* and *L. pennellii* are probed with the 750 bp mitochondrial clone, hybridization to other fragments is observed after long exposures of the blots to film (FIG. 7A). These results indicate that the mitochondrial clone hybridizes to other regions of nuclear DNA. This is also supported by the results of an analogous hybridization experiment in which total DNA digests of six F2 progeny of a cross between *L. esculentum* X *L. pennellii* were probed (FIG. 7B). Since all of the progeny have the same cytoplasm, the differences in patterns between the indivudal progeny is most likely due to segregation of nuclear fragments.

The presence of the mitochondrial homologous region within the upstream region of the $S_2$ gene indicates that it has a function in the regulation of expression of that gene. The presence of the homolog in mitochondrial DNA could indicate the presence of a similarly regulated cytoplasmic gene associated with the mechanism of gametophytic self-incompatibility. Although a cytoplasmic component is not usually associated with self-incompatibility, there are certain aberrations of the system such as the generation of new allelic specificities that appear first in the stylar (maternal) tissue that might be explained by such a cytoplasmic component.

Synthesis of S-protein in heterologous in vivo expression systems

The S-protein DNA coding sequences whose isolation is described herein can be used to direct synthesis of significant amounts of active S-protein.

The DNA encoding the S-protein can be inserted into a recombinant vector so that it is under the control of its own regulatory sequences, an endogenous regulatory region of the vector or an inserted regulatory region by conventional recombinant DNA techniques. The choice of recombinant vector is not crucial. A partial list of vectors includes lambda or M13 bacteriophage, Ti or Ri-plasmids of Agrobacterium, pBR322 derived plasmids, and plant viral vectors such as brome mosaic virus (BMV) or tobacco mosaic virus (TMV). An appropriate host microorganism or plant cell is then transformed with the vector containing S-protein coding sequences. Transformed organisms or cells are selected by conventional means and assayed for the expression of active S-protein, for example in an in vitro pollen tube inhibition assay or by immunoassay. Transformants which produce active protein can then be grown in liquid medium for an appropriate time to allow synthesis of S-protein which is then isolated and subjected to further purification, if necessary. S-protein sequences can be maintained on the vector or integrated into the chromosomal DNA of the host, where the S-protein sequences will be flanked by DNA sequences of the host.

Yeast expression systems are particularly useful for the expression of plant proteins since correct post-translational processing of plant proteins has been observed in such systems. Detailed descriptions of the expression of plant proteins in yeast are given in Rothstein, S. J. et al. (1984) Nature 308:662-665; Langridge, P. et al. (1984) EMBO J. 3:2467-2471; Edens, L. et al., 1984, supra; and Cramer, J. A. et al. (1985) Proc. Natl. Acad. Sci. 82:334-338.

Alternatively, plant proteins can be expressed using similar techniques in bacteria as exemplified in Edens, L. et al. (1982) Gene 18:1-12, which described the expression of the plant protein thaumatin in *Escherichia coli*. When a bacterial system is employed, the DNA encoding the S-protein should be free of introns, as will be the case with cDNA.

While the presence of a complete signal sequence is not essential to obtain expression of active protein in either yeast or bacteria, more efficient protein synthesis has been observed in yeast when signal sequences are present (Edens, L. et al., 1984, supra).

Reglated expression of proteins in reproductive tissue of self-incompatible plants In situ hybridization experiments in *N. alata* described in Cornish et al. (1987) Nature 326:99-102 have established that the gene encoding the S-protein is expressed throughout the female secretory tissue, the stigma, style transmitting tissue and the epidermis of the placenta. More recently, we have found in similar in situ hybridization experiments of pollen and anther sections that the S-genes of *N. alata* are expressed in pollen. The 5' non-coding regions of the S-genes thus contain regulatory sequences which direct expression of downstream coding sequences in reproductive tissue of self-incompatible plants. These regulatory sequences can be employed to selectively express a desired protein in plant reproductive tissue. Selective expression can be accomplished by the construction of chimaeric genes in which a desired structural gene is placed under the regulatory control of the S-gene regulatory sequences. Such chimaeric genes can then be introduced into plant cells or tissue regenerable into whole plants, where the desired structural gene is selectively expressed in reproductive tissue.

Example 1: Sources of Plant Materials

Seeds of heterozygous genotypes $S_2S_3$ and $S_1S_3$ of *N. alata* were provided by Dr. K. K. Pandey (Grasslanas, Palmerston North, New Zealand) and genotype $S_6S_7$ was a gift of Dr. G. Breidemeijer (Stichting Ital., Wageningen, The Netherlands). *L. peruvianum* heterozygous genotypes $S_1S_2$ and $S_1S_3$ were obtained from the Victoria State Department of Agriculture, Burnley, Victoria, Australia. Plants homozygous for the $S_2$-, $S_3$- and $S_6$-alleles were generated by bud self-pollination as described in U.S. patent application Ser. Nos. 615,079 and 050,747. Briefly, buds generated from *N. alata* heterozygous plants were emasculated at the elongated bud stage by carefully slitting the corolla with fine forceps and gently removing the immature anthers. Twenty-four hours after emasculation, just prior to the development of petal coloration, the immature stigma were pollinated with self pollen from a mature dehisced anther of another flower. Prior to pollination, the stigma surface was coated with either (i) exudate from a mature stigma (applied by gently touching the two stigma together) or (ii) 15% sucrose in 0.001% borate (applied by carefully touching the stigma to a drop of solution). After this treatment, stigma were pollinated by gently touching them into a glass Petri dish containing mature pollen or by carefully brushing pollen onto the stigma surface. To prevent premature flower drop the flower axis was smeared with a little 1% (w/w) indole acetic acid in raw lanoline. The genotypes of F1 progeny of bud-pollinated plants were established by test crossing against plants of known self-incompatibility genotype.

*B. oleracea* mixed genotype, *L. esculentum* (tomato) cv. Grosse-Lisse and *L. pennellii* (LA716) (a wild relative of tomato which was obtained from C. M. Rick, University of California, Davis, Calif.) were employed in hybridization experiments.

Mature non-pollinated styles were obtained from flowers that had been emasculated at the onset of petal coloration or from yellow buds. These mature styles were removed and used immediately or stored at −70° C. Styles refer to stigmas and style which were excised together. Ovary was separated from styles. Green bud styles refer to immature styles before the onset of self-incompatibility. cl Example 2: Purification of 32K $S_2$-protein from *Nicotiana alata* styles Flowers from *N. alata* (genotype $S_2S_3$) were emasculated at the onset of petal coloration. Two days later, the fully mature styles were removed and stored at −70° C. (Styles refer to the style and stigma which were removed together; ovary is not included.) Frozen styles (3g) were ground to a fine powder in liquid nitrogen using a mortar and pestle; this was followed by further grinding in 50 ml of extracting buffer (50 mm Tris-HCl, pH 8.5, 1 mM $CaCl_2$, 20 mM NaCl, 1 mM DTT, 10 mM EDTA and 1% (w/w) insoluble polyvinylpyrollidone. The homogenate was centrifuged (12,000 g; 15 minutes) and the supernatant (11 ml) was collected.

Prior to ion exchange chromatography the style extract (11 ml) was equilibrated with $NH_4HCO_3$ (5 mM, pH 8.6), NaCl (1 mM), CaC12 (1 mM), EDTA (1 mM) by passage through a Sephadex G-25 (Trademark, Pharmacia Inc., Uppsala, Sweden) column (1.6 cm diameter; 22 cm long, void volume 11 ml). The first 16 ml eluted after the void volume was collected and applied to DEAE-Sepharose (Trademark, Pharmacia Inc., Uppsala, Sweden) (bed volume 26 ml, 1.6 cm diameter×13 cm long) which was equilibrated with the same ammonium bicarbonate buffer. The column was then washed with this buffer (50 ml) before the application of a NaCl gradient (0–0.5 M). The $S_2$-protein was present in the unbound fractions which were combined and concentrated to a final volume of 16 ml by rotary evaporation at room temperature. The $S_2$-protein was further purified by affinity chromatography using ConA-Sepharose (Trademark, Pharmacia Inc. Uppsala, Sweden) followed by gel filtration. ConA-Sepharose was washed with 5 volumes of methyl-α-D-mannoside (0.1M) in buffer: sodium acetate (10 mM, pH 7), 0.1 M NaCl, 1 mM MgC12, 1 mM $CaCl_2$, 1 mM $MnCl_2$. The washed ConA-Sepharose was then transferred to bicarbonate buffer, $NaHCO_3$ (0.25 M, pH 8.8) for 1 hour at room temperature; the bicarbonate buffer was changed 4 times during the 1 hour period. Four volumes of $NaHCO_3$ (0.25 M, pH 8.8) containing 0.03% (v/v) glutaraldehyde were added and the ConA-Sepharose was then washed with $NaHCO_3$ (0.1M, pH 8.0), containing 0.5M NaCl, resuspended in buffer: sodium acetate (10 mM, pH 7), 0.1 M NaCl, 1 mM MgCl$_2$, 1 mM CaCl$_2$, 1 mM MnCl$_2$ and packed into a column (0.8 cm diameter, 14 cm long). The unbound fraction from DEAE-Sepharose was equilibrated in 10 mM acetate buffer, by passing through a G25-Sephadex column equilibrated with 10 mM acetate buffer, then applied to the column. Unbound material was collected, the column washed with 10 volumes of acetate buffer, and the bound material eluted with 0.1 M or 0.2 M methyl-α-D-mannoside in acetate buffer. Fractions containing S$_2$-protein were identified by sodium dodecyl sulfate polyacrylamide gel electrophoresis (SDS-PAGE), collected and concentrated to 1 ml by rotary evaporation. The use of a lower pH buffer represents an improvement over the method described in U.S. patent application Ser. No. 615,079, and results in improved yields of purified S$_2$-protein. The protein appears to be more stable at lower pH.

The pooled fraction eluted by 0.1M methyl-α-Dmannoside was applied to a column of Biogel P150 (Trademark, Biorad Laboratories, Richmond, Calif.) to separate the methyl-S-D-mannoside from the S$_2$-protein. (Void volume 13 ml, 1.6 cm diameter, 36.5 cm long equilibrated and run in NH$_4$HCO$_3$ (10 mM, pH8.5), 10 mM EDTA, 0.1M NaCl and 1 mM CaCl$_2$. A further passage through Biogel P2 (Trademark, Biorad Laboratories, Richmond, Calif.) in water was used to remove any trace of methyl-o-D-mannoside. The purified S$_2$-protein was essentially homogenous by the criteria of SDS-PAGE (FIG. 2a).

SDS-PAGE was performed according to Laemli, U.K. and Avre, M. (1973) J Mol. Biol. 80:575-583, using 12.5% (w/v) acrylamide. Samples were reduced in 1.43 M 2-mercaptoethanol in sample buffer with heating for 2 minutes in a boiling water bath. After electrophoresis, gels were stained with Coomassie Blue.

Example 3: N-terminal amino acid sequence of the *N. alata* S$_2$-protein

N-terminal sequencing was performed using an Applied Biosystems (Pfungstadt, West Germany) Model 470A gas phase sequencer. Approximately 200 μg purified S$_2$-glycoprotein was applied in aqueous solution to a glass fibre disc and evaporated to dryness. The disc was placed in the reaction cell of the sequencer, the protein was eluted and then subjected to 20 cycles of automated Edman degradation by phenylisothiocyanate procedure. The resultant amino acid phenylthiohydantoin derivatives were identified by HPLC techniques on an IBM-CN column (IBM, Danbury, Conn.) at 32° C. using a sodium acetate-acetonitrile gradient, 20 mM sodium acetate (pH 5-5.6) varying from 100%-65% (v/v) over 30 minutes. The identity of derivates was confirmed by comparison to known standard reference compounds.

Example 4: Comparison of the delgycosylated S$_2$ genotype associated style glycoprotein with the in vitro translation products of style and ovary poly(A+) RNA Frozen mature styles of *Nicotiana alata* (S$_2$S$_3$ genotype) were ground to a fine powder in liquid nitrogen using a mortar and pestle. Protein was extracted from this tissue and the S$_2$-allele associated glycoprotein was isolated by a combination of ion-exchange and affinity chromatography (U.S. patent application Ser. Nos. 615,079 and 050,747). This material was deglycosylated using a trifluoromethane sulphonic acid (TFMS) procedure modified for use with small quantities of protein (Edge et al. (1981) Anal. Biochem. 118:131-137).

Purified S$_2$-associated glycoprotein (200 μg) was lyophilized in a 10 ml glass tube with Teflon-lined screw cap and dried over P2O5 in a desiccator for 18 hours. Anisole (60 μl) and TFMS (120 μl) were added and the tube was flushed with N$_2$ for 30 seconds and sealed. After 90 minutes at 25° C., 10 ml of a 1:9 mixture of n-hexane:diethyl ether, precooled on dry ice, was added. The solution was placed on dry ice for 60 minutes, centrifuged (500 g, 5 minutes, 4° C.) and the supernatant discarded. The pellet was air-dried, resuspended in buffer (300 μl) and the pH was adjusted to 6.8 by addition of pyridine:H20 (1:1). The sample was boiled for 2 minutes before electrophoresis.

Total RNA was isolated from ovary, green bud style or mature style by conventional methods using guanidinium thiocyanate as a protein denaturant. Oligo(dT)-cellulose chromatography was used to isolate mRNA which is polyadenylated, poly(A+) RNA. This poly(A+) RNA (2.0 or 0.5 μg) was translated using an amino acid depleted rabbit reticulocyte lysate kit (Amersham, Arlington Heights, Illinois) in the presence of 150 mM K$^+$, 1.2 mM Mg$^{2+}$ and tritiated amino acids. Leucine, lysine, phenylalanine, proline and tyrosine were used at specific activities of 5.4, 3.1, 4.8, 3.8 and 4.0 TBq/mmol, respectively. The reaction volume was 25 μl. After incubation for 90 minutes at 30° C., RNA was removed by treatment with bovine pancreatic ribonuclease (5 μl, 2 mg/ml) for 20 minutes at 37°.

The glycosylated and deglycosylated samples of pure S$_2$-allele protein were analyzed by SDS-polyacrylamide gel electrophoresis (SDS-PAGE) using 15% acrylamide. The gels were stained with Coomassie Blue.

Similarly, the translation products of mature style poly(A+) RNA were separated by SDS-PAGE using 10-15% acrylamide gradient gels. The products were visualized after treatment of the gel with Amplify (Trademark, Amersham, Arlington Heights, Ill.) and exposure to X-ray film. In both cases, molecular weight markers were included in adjacent lanes and visualized with Coomassie Blue.

EXAMPLE 5: PREPARATION OF A cDNA LIBRARY IN BACTERIOPHAGE λgt 10

Poly(A+) RNA was isolated from mature styles of *N. alata* (genotype S$_2$S$_3$) as described above and transcribed into double stranded cDNA (Maniatis et al., 1982, supra). Blunt-ended cDNA was prepared by end repair with DNA polymerase. EcoRI sites contained in the cDNA were blocked by treatment with EcoRI methylase. Synthetic EcoRI linkers were then ligated to the double stranded cDNA. The cDNA was then cloned into the EcoRI site of λgt10 as described by (Huynh, et. al., 1985, supra). This phage was used to infect *Escherichia coli* C600 and plated.

Example 6: Differential screening of mature style cDNA library

Poly(A+) RNA was isolated from mature style, green bud style or ovary of *N. alata* genotype S$_2$S$_3$. Single stranded $^{32}$P-labelled cDNA hybridization probes were prepared by random priming from the individual RNA. Lambda gt10 containing the mature style library was used to infect i E. coli C600 and plated at a density of about 1000 plaque forming units/150 mm Petri plate. Duplicate nitrocellulose lifts were prepared for hybridization (Maniatis et al., 1982, supra). The plaques were first screened with labelled cDNA probe from mature style and green bud style. Plaques that hybridized strongly only to the mature style probe were selected, picked, purified and subjected to a second differential screening using the probes to mature style and ovary. The resultant plaques represent mature style specific clones.

In these plaque hybridizations, the filters were treated prior to hybridization (prehybridized) for 2 hours and during hybridization for 16 hours at 42° C. with 5× Denhardt's solution, 5× SSC (3 M NaCl, 0.3M Trisodium citrate), 50 g/ml sonicated salmon sperm DNA, 50 mM sodium phosphate (pH 6.8), 1 mM sodium pyrophosphate, 100 μM ATP and 50% deionized formamide. Probes were used at a specific activity of $4 \times 10^7$ cpm/ml Filters were washed in a 0.1× SSC solution containing 0.1% SDS (sodium dodecyl sulfate) at 42° C.

EXAMPLE 7: ISOLATION OF THE cDNA CLONES SPECIFIC FOR THE $S_2$-ALLELE ASSOCIATED PROTEIN

A set of 24 14-mer oligonucleotides was synthesized corresponding to all possible codon ambiguities at amino acids 4–8 in the N-terminal sequence of the $S_2$-protein (Table 1). Oligonucleotides were synthesized by the solid-phase phosphoramidite methodology (Beaucage and Caruthers, (1981) Tetrahedron Letters 22:1859) using an Applied Biosystems (Pfungstadt, West Germany) ABI Model 80A DNA synthesizer. The 14-mers were end labelled using T4 kinase in the presence of $^{32}$P-ATP (5000 Ci/mmol). These labelled 14-mers (5 μg/ml) were used in three batches of 8 14-mers to prime selective cDNA synthesis using mature style poly(A+) RNA. Reverse transcription reaction volume was 40 μl. The reaction contained 0.75 mM of dCTP, dGTP, dTTP and dATP, 75 μg/ml poly(A+) RNA, 50 mM Tris-HCl (pH 8.3), 10 mM KCl, 8 mM, MgCl2, 0.4 mM dithiothreitol, 500 U/ml placental RNAase inhibitor and 500 U/ml AMV reverse transcriptase. After incubation at 42° C. for 90 minutes, the reactions were stopped by addition of EDTA to 50 mM, extracted with phenol:chloroform 1:1 (v/v) and the product, labelled cDNA, was precipitated with ethanol. The pellets were resuspended in 20 μl of a solution of 100 mM NaOH, 7M urea, and 10 mM EDTA. Samples were heated at 90° C. for 5 minutes before electrophoresis on an 8% (w/v) acrylamide/7 M urea gel. The gel was exposed to X-ray film for 5 minutes, to locate specifically primed cDNA products As shown in FIG. 4, one of the batches of synthetic 14-mers primed synthesis of a 100 bp nucleotide specific cDNA for mature style. This 100 bp nucleotide cDNA band was excised from the gel and eluted overnight with shaking at 37 C in 0.5M ammonium acetate and 1 mM EDTA. The elutant was concentrated by butanol extraction, phenol:chloroform extracted and ethanol precipitated. The 100 bp nucleotide was then sequenced using the technique of Maxam and Gilbert (1977), Proc. Natl. Acad. Sci. 74:560. The sequence of this nucleotide corresponded to the −12 to +8 amino acid of the $S_2$-protein is shown in Table 2.

A 30 bp-long synthetic oligonucleotide probe based on the sequence of the 100 bp cDNA and covering the region −8 to +1 of the corresponding amino acid sequence was prepared as described above. The 30-mer probe was end-labelled with $^{32}$P-ATP. This probe was then used to screen the mature style specific clones obtained by differential screening of the λgt10 library. The hybridization of the $^{32}$P-labelled oligomer probe ($4 \times 10^7$ cpm/ml) was done as described above except that the formamide concentration was decreased to 20% and the temperature was decreased to 37° C. Filters were washed using 2× SSC at 37° C. Approximately 100,000 plaques from two separately prepared libraries were screened yielding 5 clones that strongly hybridized with the 30-mer probe. One λgt10 clone, designated NA-2-1, was selected for further study. This clone was found to contain a single 877 bp insert which could be excised from the lambda vector by EcoRI digestion. After sequencing of the NA-2-1 clone, it was found that an error had been made in reading the sequencing gel of the 100 bp fragment. The sequence shown in Table 2 was used to prepare the 30-mer probe. The sequence of the 30-mer probe that was used in screening did not therefore exactly correspond to the NA-2-1 clone insert.

Example 8: Nucleotide sequence of NA-2-1 cDNA insert

The excised 877 bp DNA insert was sequenced using the chain termination method (F. Sanger et al. (1977) Proc. Natl. Acad. Sci. USA 74:5463–5467; Sanger et al. (1980) J. Mol. Biol. 143:161–178). The NA-2-1 clone insert was found to contain the full $S_2$ gene coding sequence but the sequence did not extend at the 5' end to an ATG codon.

This clone insert contained a nearly full length $S_2$ gene cDNA. The full sequence of the NA-2-1 clone is not provided, this sequence was provided in U.S. patent application Ser. Nos. 792,435 and 854,139. The sequence of the subsequently isolated full-length clone NA-2-2 (see below) is provided in Table 3 and the sequence differences in the 3'-region of the two clones are indicated therein. In the sequencing of the NA-2-1 insert, a stop codon was identified in the middle of what was believed to be the protein coding sequence. Protein sequencing of the polypeptide fragment corresponding to the coding region in question revealed that an extra adenine nucleotide has been inserted in the region 171–182 of the clone, most likely as a result of a sequencing artifact.

EXAMPLE 9: NORTHERN BLOT ANALYSIS

A $^{32}$P-labelled probe was prepared from the cDNA clone (NA-2-1) insert encoding the $S_2$-allele associated protein by random priming. Aliquots of poly(A+) RNA were fractionated on formaldehyde −1.2% (w/v) agarose gels as described by Maniatis, et al. (1982) supra. except that the gel was run in 20 mM morpholinopropane sulfonic acid (pH 7.0), 5 mM sodium acetate and 0.1 mM EDTA (pH 8.0) as a buffer. The gel was blotted directly onto nitrocellulose filters using 20X SSC. Klenow labelled-HindIII EcoRI lambda fragments were used as molecular weights markers. Prehybridization and hybridization were carried out at 42. as described for plaque hybridization.

Example 10: Cloning and sequencing of the nearly full length $S_2$-protein clone from NA-2-1 into M13mp8

The 877 bp NA-2-1 clone insert was excised from λgt10 with EcoRI restriction endonuclease. The DNA fragments generated were precipitated with ethanol, dried in vacuo and resuspended in water, to 0.25 μg The DNA/μl. The DNA fragments (2.5 μg) were then subjected to end repair by incubation at 37° C. for 1 hour in 25 μl buffer containing: 2 mM each of dATP, dCTP, dGTP and dTTP, 10 units DNA polymerase I (Klenow fragment), 50 mM Tris-HCl (pH 7.6), 10 mM MgCl$_2$ and 10 mM dithiothreitol. The end-repaired fragments were reprecipitated, dried in vacuo and again suspended in water to 0.25 μg DNA/μl.

The end repaired fragments were inserted into the commercially available vector M13mp8 which had been cut with SmaI restriction endonuclease and dephosphorylated (Amersham, Arlington Heights, Illinois). Blunt-end ligation was done using 1.25 μg of the end repaired fragments and 20 ng of M13mp8 in a buffer containing 1 U/μl T4 ligase, 1 mM ATP 66 mM Tris-HCl (pH 7.6), 5 mM MgCl$_2$ and 5 mM dithiothreitol. The ligation mixture (total volume of 20 μl) was incubated overnight at 4° C.

The ligation mixture (10 μl) was then used to transform 0.2 ml of competent E. coli JM101 cells (Messing, J. et al. (1981) Nucleic Acids Res. 9:309). Clones containing the 877 bp $S_2$-protein DNA fragment were identified using the purified 877 bp $S_2$-clone insert labeled with $^{32}$P by random priming as a hybridization probe. DNA was purified from one of the selected clones and a DNA molecule designated pAEC5 was isolated which consisted of the 877 bp fragment inserted in the SmaI site of M13mp8.

Mature style poly(A+) RNA was used to prepare a second cDNA library in λgt10. The library was constructed according to a method described by Okayama et al. (1982) Mol. Cell Biol. 2:161–170, which was designed to optimize isolation of full-length cDNA clones. A library containing 20,000 plaques was obtained from 5 μg of poly(A+) RNA. This library was screened as described in Example 6 using the 30-bp long synthetic oligonucleotide probe as well as the 877 bp cDNA insert from the NA-2-1 clone of Example 7. One clone, designated NA-2-2, which hybridized to both probes, was selected for further study.

The NA-2-2 cDNA insert was sequenced using the same methods employed to sequence the NA-2-1 insert. Table 3 shows the sequence of the NA-2-2 cDNA insert which contains the full structural coding region for the mature $S_2$-protein which is identical to that of the NA-2-1 except that there in no extra adenine nucleotide in the NA-2-2 clone sequence. The NA-2-2 clone also encodes the full signal sequence, which extends 22 amino acids on the N-terminal end of the mature protein. The derived amino acid sequence of the signal peptide of both NA-2-1 and NA-2-2 is identical up to amino acid −18. The reason for the discrepancy in sequence at the 5'-end between the two clones is believed to be the result of a sequencing artifact. The two clones are different in the length of their 3' untranslated sequence. They are identical to the polyadenylation site in clone NA-2-2. The NA-2-1 clone contains an extra 50 necleotides before the poly(A) tail.

Example 11: Isolation of N. alata $S_6$ and $S_6$ cDNA clones cDNA libraries of genotypes $S_3S_3$ and $S_6S_6$ were prepared in λgt10 using mRNA from mature styles as described in Example 4. Single stranded $^{32}$-P-labelled cDNA hybridization probes were prepared by random priming from the individual RNA. Plaque hybridization screens were performed essentially as described in Example 4.

The $S_3$-clones were selected by differential screening of the $S_3S_3$ cDNA library with $S_3S_3$ cDNA and $S_6S_6$ labelled cDNA. Plaques that hybridized strongly to $S_3S_3$ cDNA and weakly to $S_6S_6$ cDNA were selected and rescreened with the labelled $S_2$ cDNA clone (NA-2-1 or NA-2-2). Clones which hybridized to the $S_3S_3$ cDNA and the $S_2$ cDNA clone were then used as probes of northern blots containing RNA from several N. alata S-genotypes. Clones which hybridized most strongly to RNA from styles which carry the $S_3$-allele, and weakly to RNA from styles which do not carry the $S_3$-allele are selected as $S_3$ clones. The DNA sequence of one $S_3$ clone selecteed by this procedure is provided in Table 4.

The $S_3$ clone selected for sequencing was near full-length but during subcloning into the pGEM vector for sequencing, a short EcoRI fragment at the 5' end of the clone was inadvertently deleted. Sequence extending 5' to the indicated EcoRI was determined by RNA sequencing and the N-terminal amino acid sequence was obtained by microsequencing analysis.

$S_6$ cDNA clones were obtained using a similar differential screening procedure. Plaques were initially selected if they hybridized strongly to $S_6S_6$ cDNA and poorly to $S_3S_3$ cDNA. The DNA sequence of one $S_6$ clone selected by this procedure is provided in Table 5. This clone contained the entire $S_6$ gene coding sequence, but does not extend in the 5' direction to an ATG codon and so is not full length. Furthermore, the sequenced $S_6$ clone does not contain a poly(A) tail.

Example 12: Isolation and characterization of the chromosomal $S_2$ gene

Genomic DNA of the N. alata $S_2S_2$ genotype was isolated from leaves essentially as described in Bernatzky and Tanksley, 1986, suora. The $S_2$ cDNA clone was radioactively labelled and employed as a hybridization probe of Southern blots of EcoRI digested $S_2S_2$ DNA. The $S_2$ gene probe hybridized to a single approximately 3.1 kb EcoRI fragment. This fragment was isolated and cloned in λgt10 following ligation of EcoRI digested λgt10 with size fractionated (2.5–4.0 kb EcoRI fragment. The 3.1 $S_2$ gene fragment was sequenced and the sequence is given in Table 6. The fragment includes an open reading frame extending from nucleotide 1603 to 2338 Which is interrupted by a single 94 bp intron (nucleotides 1833–1927). The sequence includes the two polyadenylation signals ($T_1$ and $T_2$) which had been identified in the two $S_2$ cDNA clones. Conventional primer extension techniques were employed to map the starting point of transcription to a "G" base 19 bp upstream of the ATG start codon. Sequence analysis identified a putative "TATA" box (nucleotides 1549–1559) in the 5' upstream region of the gene.

Analysis of the 5' non-coding region of the $S_2$ genomic clone

Subclones of the 3.1 kb EcoRI $S_2$ gene fragment were generated with HincII. An approximately 1.0 kb subfragment extending 5' from nucleotide 1249 (Table 6) was used to probe Southern blots of total DNA from N. alata and L. esculentum digested with HindIII. As shown in FIG. 6A, this probe produced a highly repeated pattern on N. alata DNA but hybridized to only one major band (approximately 750 bp) of L. esculentum DNA. Mitochondrial DNA was then isolated from N. alata and L. esculentum using the DNAse I procedure (Kalodner and Tweari (1972) Proc. Natl. Acad. Sci. USA 69:1830–1834). Southern blots of mitochondrial DNA were also probed with the approximately 1.0 kb nuclear DNA fragment (FIG. 6A). A comparison clearly indicates that the 1 kb fragment contains a region that is homologous to mitochondrial DNA of both N. alata and L. esculentum.

Mitochondrial DNA of alata was digested with HindIII and ligated into the bacterial plasmid vector pGEM (Promega Biotec, Madison, Wis.) using $T_4$ DNA ligase and transformed into E. coli JM109. The 750 bp homologous fragment was identified by screening colony lifts with the approximately 1.0 kb HincII fragment of the $S_2$ gene. The mitochondrial DNA fragment was isolated and sequenced. The isolated 750 bp mitochondrial DNA fragment was then radioactively labelled and used as a probe of Southern blots of total and mitochondrial DNA of N. alata and L. esculentum (FIG. 6B). The mitochondrial DNA fragment hybridized to a single fragment in total DNA of both N. alata and L. esculentum. The repeated pattern of hybridization to total DNA of N. alata in FIG. 6B is apparently due to sequences in the 1 kb genomic clone outside of the mitochondrial DNA homologous segment.

The 750 bp fragment was digested with HincII, blotted and probed with the 1.0 kb genomic fragment to estimate the length of homology. The homologous sequence was found to occur on a 315 bp HindIII/HincII fragment which was cloned into pGEM and sequenced (Table 7). Alignment of the mitochondrial and 1.0 kb $S_2$ gene fragment sequences (Table 7) reveals a highly homologous 56 bp segment. Two additional short, perfectly matched sequences are also found 3' to the 56 bp segment. The spacing of the matched sequences is different in the mitochondrial and nuclear sequences. In addition the nuclear sequence contains a short 8 bp direct repeat that immediately flanks the 5' region of homology.

When Southern blots of total DNA of N. alata, L. esculentum and L. pennellii probed with the 750 bp mitochondrial clone are subjected to long exposures to film (FIG. 7A), several other fragments are found to hybridize to the probe. These fragments are believed to be nuclear DNA. Other evidence that the 750 probe hybridizes to nuclear DNA comes from an analysis of F2 progeny of a cross between L. esculentum and L. pennellii. Samples of total DNA from six progeny were digested with EcoRI and probed with the 750 bp fragment (FIG. 7B). The differences observed in the hybridization patterns among the F2 progeny is most likely due to segregation of nuclear fragments since the progeny have the same cytoplasm.

In these experiments, Southern blots were produced from restriction fragments that were separated on 0.9% agarose gels, treated for 12 minutes in 0.25 NHCl and transferred to Zelaprobe nylon membrane (Biorad, Richmond, Calif.) in 0.4M NaOH. Probes were made by random priming of inserts. Filtes were hybridized at 68° C. overnight and were washed to a final stringency of 1× SSC, 0.1% SDS at 68° C.

Those skilled in the art will appreciate that the invention described herein and the methods of isolation and identification specifically described are susceptible to variations and modifications other than as specifically described. It is to be understood that the invention includes all such variations and modifications which fall within its spirit and scope.

TABLE 1

Comparison of N-terminal Amino Acid Sequences of Gametophytic S-proteins[a]

| | pI | Mr | Amino-terminal sequence | | | | | | | | | | | | | | |
|---|---|---|---|---|---|---|---|---|---|---|---|---|---|---|---|---|---|
| | | | 1 | 2 | 3 | 4 | 5 | 6 | 7 | 8 | 9 | 10 | 11 | 12 | 13 | 14 | 15 |
| L. peruvianum | | | | | | | | | | | | | | | | | |
| $S_1$ | 7.5 | 28000 | Y | F | E | Y | L | Q | L | V | L | Q | X | P | T | T | F |
| $S_3$ | >9.5 | 28000 | D | F | D | Y | L | Q | L | V | L | Q | X | P | R | S | F |
| N. alata | | | | | | | | | | | | | | | | | |
| $S_2$ | >9.5 | 32000 | A | F | E | Y | M | Q | L | V | L | T | W | P | I | T | F |
| $S_6$ | >9.5 | 31000 | A | F | E | Y | M | Q | L | V | L | Q | W | P | T | A | F |
| $S_z$ | 9.0 | 30000 | D | F | D | Y | M | Q | L | V | L | T | X | P | A | S | F |
| $S_{f1}$ | 9.5 | 27000 | D | F | E | Y | L | Q | L | V | L | T | W | P | A | S | F |
| $S_3$ | | | A | F | E | Y | M | Q | L | V | L | Q | W | P | A | A | F |

[a]Amino acids are identified by their single-letter code, with X indicating residues which could not be clearly assigned. Residues which are identified in all six proteins are boxed. Sequences of L. peruvianum $S_1$ and $S_3$ and the N. alata $S_2$ and $S_{f1}$ are from Clarke et al., U.S. Pat. application Ser. Nos. 615,079 and 854,139.

TABLE 2

Partial nucleotide sequence of 100 bp cDNA fragment

```
−12  −11  −10  −9   −8   −7   −6   −5   −4   −3
Phe  Ile  Leu  Leu  Cys  Ala  Leu  Ser  Pro  Ile
TTC  ATT  TTG  CTT  TGT  GCT  CTT  TCG  CCG  ATT

−2   −1    1    2    3    4    5    6    7    8
Tyr  Gly  Ala  Phe  Glu  Tyr  Met  Gln  Leu  Val
TAT  GGG  GCT  TTC
```

30 mer probe sequence

3'-GAA ACA CGA GAA AGC GGC TAA ATA CCC CGA-5'

TABLE 3

Nucleotide sequence of the full-length cDNA coding for the 32K molecular weight $S_2$-protein of Nicotiana alata.[1]

```
       Met Ser Lys Ser Gln Leu Thr Ser Val Phe Phe Ile
GACGGA ATG TCT AAA TCA CAG CTA ACG TCA GTT TTC TTC ATT
  −70         −60         −50         −40

Leu Leu Cys Ala Leu Ser Pro Ile Tyr Gly Ala Phe Glu Tyr Met Gln Leu Val Leu Thr
TTG CTT TGT GCT CTT TCA CCG ATT TAT GGG GCT TTC GAG TAT ATG CAA CTC GTG TTA ACA
 −30         −20         −10          1          10          20          30
```

TABLE 3-continued

Nucleotide sequence of the full-length cDNA coding for the 32K molecular weight S₂-protein of *Nicotiana alata*.[1]

```
Trp Pro Ile Thr Phe Cys Arg Ile Lys His Cys Glu Arg Thr Pro Thr Asn Phe Thr Ile
TGG CCA ATC ACT TTT TGC CGC ATT AAG CAT TGC GAA AGA ACA CCA ACA AAC TTT ACG ATC
        40          50          60          70      .   80          90

His Gly Leu Trp Pro Asp Asn His Thr Thr Met Leu Asn Tyr Cys Asp Arg Ser Lys Pro
CAT GGG CTT TGG CCG GAT AAC CAC ACC ACA ATG CTA AAT TAC TGC GAT CGC TCC AAA CCC
        100         110         120         130         140         150

Tyr Asn Met Phe Thr Asp Gly Lys Lys Lys Asn Asp Leu Asp Glu Arg Trp Pro Asp Leu
TAT AAT ATG TTC ACG GAT GGA AAA AAA AAA AAT GAT CTG GAT GAA CGC TGG CCT GAC TTG
        160         170         180         190         200         210

Thr Lys Thr Lys Phe Asp Ser Leu Asp Lys Gln Ala Phe Trp Lys Asp Glu Tyr Val Lys
ACC AAA ACC AAA TTT GAT AGT TTG GAC AAG CAA GCT TTC TGG AAA GAC GAA TAC GTA AAC
        220         230         240         250         260         270

His Gly Thr Cys Cys Ser Asp Lys Phe Asp Arg Glu Gln Tyr Phe Asp Leu Ala Met Thr
CAT GGC ACG TGT TGT TCA GAC AAG TTT GAT CGA GAG CAA TAT TTT GAT TTA GCC ATG ACA
        280         290         300         310         320         330

Leu Arg Asp Lys Phe Asp Leu Leu Ser Ser Leu Arg Asn His Gly Ile Ser Arg Gly Phe
TTA AGA GAC AAG TTT GAT CTT TTG AGC TCT CTA AGA AAT CAC GGA ATT TCT CGT GGA TTT
        340         350         360         370         380         390

Ser Tyr Thr Val Gln Asn Leu Asn Asn Thr Ile Lys Ala Ile Thr Gly Gly Phe Pro Asn
TCT TAT ACC GTT CAA AAT CTC AAT AAC ACG ATC AAG GCC ATT ACT GGA GGG TTT CCT AAT
        400         410         420         430         440         450

Leu Thr Cys Ser Arg Leu Arg Glu Leu Lys Glu Ile Gly Ile Cys Phe Asp Glu Thr Val
CTC ACG TGC TCT AGA CTA AGG GAG CTA AAG GAG ATA GGT ATA TGT TTC GAC GAG ACG GTG
        460         470         480         490         500         510

Lys Asn Val Ile Asp Cys Pro Asn Pro Lys Thr Cys Lys Pro Thr Asn Lys Gly Val Met
AAA AAT GTG ATC GAT TGT CCT AAT CCT AAA ACG TGC AAA CCA ACA AAT AAG GGG GTT ATG
        520         530         540         550         560         570

Phe Pro ***
TTT CCA TGA TTAATAATATTTGTTTTATTGCATTATGCCATGTAAAAAAAAATTCAAAACCTCAAGTATAAACGTG
        580         590         600         610         620         630         640

TAATCAAGACTATTAAGCACGCACTTATTGAAGACTAAAAAAAAAAAAAAAAAAAAA
    656         666         676
                    NA-2-1:         ACACTCGGAAGAATAAGCAAAATTCTTATCAATT
                                        686         696         706         716

TATGGAAATCGTTATTAAAAAAAAAAAAAAAAAAAAAGGGGGACGGACTGGGAACGGTTCTTCGGGGTCCCGG
    726         736         746         756         766         776         786
```

[1] The signal sequence is underlined, positive numbering begins at the first codon of the mature protein sequence. The differences in 3' end sequence between the full-length NA-2-2 clone and the near full-length clone NA-2-1 are also indicated.

TABLE 4

The nucleotide sequence of the S₃ cDNA clone.[1]

```
←signal─ A   F   E   Y   M   Q   L   V   L   Q   W   P   A   A
            ... TTA CAA TGG CCA GCA GCC
                                    147

F   C   H   T   T   P   S   P   C   K   R   I   P   N   N
TTT TGT CAC ACC ACT CCT AGT CCT TGC AAA AGA ATT CCA AAC AAC
                            174                 Eco RI

F   T   I   H   G   L   W   P   D   N   V   S   T   M   L
TTC ACA ATT CAT GGG CTT TGG CCG GAT AAC GTG AGC ACA ATG CTT
                                    219

N   Y   C   S   G   E   D   E   Y   E   K   L   D   D   D
AAT TAC TGC TGT GGC GAA GAT GAG TAC GAA AAA TTA GAT GAT GAT
                                    264

K   K   K   K   D   L   D   D   R   W   P   D   L   T   I
AAA AAG AAG AAA GAT CTG GAT GAC CGC TGG CCT GAC TTG ACA ATT
                                    309

A   R   A   D   C   I   E   H   Q   V   F   W   K   H   E
GCC CGA GCT GAT TGT ATC GAA CAT CAA GTT TTC TGG AAA CAT GAA
    354
```

TABLE 4-continued

The nucleotide sequence of the $S_3$ cDNA clone.[1]

```
     Y   N   K   H   G   T   C   C   S   K   S   Y   N   L   T
    TAC AAT AAG CAT GGA ACG TGT TGT TCC AAG AGC TAC AAT CTA ACA
                              399

Q   Y   F   D   L   A   M   A   L   K   D   K   F   D   L
    CAA TAT TTT GAT TTA GCC ATG GCC TTA AAG GAC AAA TTT GAT CTT
                              444

L   T   S   L   R   K   H   G   I   I   P   G   N   S   Y
    TTG ACA TCT CTC AGG AAG CAT GGC ATT ATT CCT GGA AAC AGT TAT
                              489

T   V   Q   K   I   N   S   T   I   K   A   I   T   Q   G
    ACC GTT CAA AAA ATC AAT AGC ACC ATA AAG GCA ATC ACG CAA GGG
                              539

Y   P   N   L   S   C   T   K   R   Q   M   G   L   L   E
    TAT CCT AAC CTC TCG TGC ACT AAA AGA CAA ATG GAG CTA TTG GAG
                              579

I   G   I   C   F   D   S   K   V   K   N   V   I   D   C
    ATA GGC ATA TGT TTC GAC TCG AAG GTA AAA AAT GTG ATA GAT TGT
                              624

P   H   P   K   T   C   K   P   M   G   N   R   G   I   K
    CCT CAT CCT AAG ACA TGC AAA CCT ATG GGA AAT AGG GGG ATT AAG
                              669

F   P   *
    TTT CCA TGA TTA TAA ATT TCT GTT TCT GTT GCT TTG AGC TGC CTA
                              714

AAA AAT AAT ACA AAA CTA ATA AGG GAT AAT CAG GAC CAT GGG ACA
                              759

ATT CTA TTA TGA AAG CCA ACA TTG TGG AAC CAT ATA TAA TTT CCA
                              804

TAT AAA TTT ATG AAA NNT ATT ATT GAA CTG ACA CTT ATT TTG TGT
                              849

CAA AAA AAA AAA AAA AAA AAA AAA AAA AAA AAA AAA AAA AAA AAA
                              899

AAA AAA AAA AA
                939
```

[1] The isolated $S_3$ cDNA clone is near full length, but part of the 5' end of the clone was removed during subcloning for sequencing due to the presence of an EcoRI site (196–201). The sequence 5' to this site was obtained by RNA sequencing. The N-terminal amino acid sequence was obtained by microsequencing analysis of the isolated $S_3$ protein.

TABLE 5

Nucleotide sequence of the $S_6$ cDNA clone[1]

```
       M   F   N   L   P   L   T   S   V   F   V   I   F   X   F   A   L   S   P   I   Y
      ATGTTTAACTTACCACTCACGTCAGTTTTCGTCATATTTNTTTTTTGCTCTTTCGCCCATTTAT
    <-signal 10          20          30          40          50          60
       1

G   A   F   E   Y   M   Q   L   V   L   Q   W   P   T   A   F   C   H   T   T
        GGGGCTTTCGAATACATGCAACTTCTTTTACAATGGCCAACCGCTTTTTGCCACACTACT
                70          80          90         100         110         120

P   C   K   N   I   P   S   N   F   T   I   H   G   L   W   P   D   N   V   S
        CCTTGCAAAAATATTCCAAGCAACTTTACAATCCATGGACTTTGGCCGGATAACGTGAGT
                130         140         150         160         170         180

T   T   L   N   F   C   G   K   E   D   D   Y   N   I   I   M   D   G   P   E
        ACAACGCTGAATTTCTGTGGTAAAGAAGATGACTATAACATTATAATGGATGGACCCGAG
                190         200         210         220         230         240

K   N   G   L   Y   V   R   W   P   D   L   I   R   E   K   A   D   C   M   K
        AAGAATGGTCTGTATGTCCGCTGGCCTGACTTGATCAGAGAGAAAGCTGATTCTATGAAA
                250         260         270         280         290         300

T   Q   N   F   W   R   R   E   Y   I   K   H   G   T   C   C   S   E   I   Y
        ACGCAAAATTTCTGGAGACGTGAATACATTAAGCATGGAACGTGTTGTTCAGAGATCTAC
                310         320         330         340         350         360
```

TABLE 5-continued

Nucleotide sequence of the S₆ cDNA clone[1]

```
  N   Q   V   Q   Y   F   R   L   A   M   A   L   K   D   K   F   D   L   L   T
AATCAAGTACAATATTTTCGTTTAGCCATGGCCTTAAAAGACAAGTTTGATCTTCTGACT
      370         380         390         400         410         420

S   L   K   N   H   G   I   I   R   G   Y   K   Y   T   V   Q   K   I   N   N
TCTTTGAAAAATCATGGAATTATTCGTGGTTACAAATATACCGTTCAGAAAATCAATAAC
      430         440         450         460         470         480

T   I   K   T   V   I   K   G   Y   P   N   L   S   C   T   K   G   Q   E   L
ACGATCAAGACAGTAACAAAAGGGTATCCTAACCTCTCGTGCACTAAAGGGCAAGAACTA
      490         500         510         520         530         540

W   E   V   G   I   C   F   D   S   T   A   K   N   V   I   D   C   P   N   P
TGGGAGGTTGGCATATGTTTCGACTCGACAGCGAAAAATGTAATTGATTGTCCTAATCCT
      550         560         570         580         590         600

K   T   C   K   T   A   S   N   Q   G   I   M   F   P   *
AAGACATGCAAAACAGCGTCGAATCAGGGAATTATGTTTCCATGAACAAAATTGGCATTT
      610         620         630         640         650         660

TTCTTGGTTTAGGCTACGTAAACCAAAATCCAAACCACACGAATAATCAAGAAAATCAAA
      670         680         690         700         710         720

CAAAATTTTATTATGAAGATCAAATTGTCAAACCATATGTAAATTTGATAACAAATTTAT
      730         740         750         760         770         780

GAAAAGTATTATTGAACTGCG
      790         800
```

[1] The S₆ cDNA clone does not extend to an ATG codon at the 5′ end and does not contain a poly(A) tail. It is believed that the clone is only 2 bases short at the 5′ end with the first nucleotide of the sequence predicted to be the last base of the ATG start codon. The predicted bases at the 5′ end of the sequence are underlined.

TABLE 6

N. alata S₂ genomic sequence

```
GAATTCACGAGAAGAAGTGTCAAAAATGTTTCTTATCATTCCTCTCTAAGAAACTCAGAGACTATTTGTA
       10        20        30        40        50        60        70

CGCGGCAAAATCGGAAGACTTTGATTTTTTGCAATCAAGACACTTCAAAGGGTTTCCCCCGAGACCCCGAG
       80        90        100       110       120       130       140

TTGGGAGGCCGTGATCGAGCACGAGCCTCGGGGCTCGACGAAGTCTGACTTAAAGGAAGCGAGTACCCGA
      150       160       170       180       190       200       210

GGTCGGGGTGGAAGAAGAAGTCTCCCAAGCACATGGCTACACCTAACAGATCCGGACTATCTAGGGCCTA
      220       230       240       250       260       270       280

CTATGATGTCCCGCATCAAGCCGTCCCATCTCTGTATTCGTTAACTTACTTGCATTTTACCTAGTCCCCT
      290       300       310       320       330       340       350

TGCCTATATAAAGGGGACTCGCCCTACCTTGTAGGAGACGGATGTTGCTCCACTTCTCCAAAATGCAATA
      360       370       380       390       400       410       420

ATATCTTTCTCTCTTTCTCTTTTCTCCAAGCTACTCGTGTTCATTGACCTCGAGGTCGCCTTAGCACTTT
      430       440       450       460       470       480       490

ACTATTTCCTTGCTTGTTTTTCGTTATTTTGCTCAATATTGATAGTATAGAGCTAGGCTCAATCGTATTT
      500       510       520       530       540       550       560

TACCAGTTATCCCCTTCCCGACCATCCTCGATAAGCCCGAGACAGGCTCGAGGCTCGGCCCCGAGGCATC
      570       580       590       600       610       620       630

CACTGGCCGGGTTTACGCCGGGGAAATGTCTCCTTACTGGTTCGATTATCGCTTTGTTTAACTCGATCTC
      640       650       660       670       680       690       700

CATCGCTTTACTTCACGCTTTAGCACTAAACACCCCCACAAACTAGCTCGGGAATAGATCACGTATTTTT
      710       720       730       740       750       760       770

AGAATACCATTTATAAATTTAATTGTTGTTACTATTTTCACGGTAAACACCTGCAAGAATCGTGAAAATA
      780       790       800       810       820       830       840

CCTATATGAGGTTGTTTACCAAGAATGTTGGTCATGATCAACCCCAACAACTTCAAAGCTTAAAAATTAA
      850       860       870       880       890       900       910

TTTTTTCTTTGCTAAATCACATTTAACATTTCTGGAAATCTAAGCGAGACACACACAAAACATAAAATCA
      920       930       940       950       960       970       980

CCAAATGAAGTTCCTCGATGTTTCAAATCATGAAATAGAAAGCTAGACTTCAAAAAAATATATCGAGTCA
      990       1000      1010      1020      1030      1040      1050
```

TABLE 6-continued

*N. alata* S₂ genomic sequence

```
                                                          ←——————————
CTAAGTACTTTTCGAATTAATTAGCATAACACAAACTTCATATCACAAAAAGTACCTATAAAAAGTATGT
     1060      1070      1080      1090      1100      1110      1120

————————————————————— Homology with mitochondrial DNA ————————————————→
CCCAACAATTTAGCCTGAAATGAAAAAAAGTGGGGTAGAAACTAAGTTTCTTTTAGATCCTTTTGAAATC
     1130      1140      1150      1160      1170      1180      1190

┌─┐
CTCATACAACTGATGGAATAAATATATGAGTCTTTAAGGAGCAAGCCATAGGTTGAGTTGACAGAAAGAA
     1200      1210      1220      1230      1240      1250      1260

GTCCATAACATATTACATGAAGAGAAAGTGGTTGTAAAACTAGCTCACAAAAATTTGCTCTGATATCACG
     1270      1280      1290      1300      1310      1320      1330

TGAATGAATATGAGCATATAACTAAAAGTTTAAAGCCATCGGAGGATAGCCCCAAAAAAAAAAATTCCAC
     1340      1350      1360      1370      1380      1390      1400

CCATTTGATAATTCTTACACCACTAACGACTGAGACGTATATTATACTTTATCATTAACAGACTAATTAG
     1410      1420      1430      1440      1450      1460      1470

GTATGAGTCTAATAGTACATACTTATCTAGACCAAAGAAAACGTGTCGAATTTGACACTTATCGACGGAT
     1480      1490      1500      1510      1520      1530      1540
```

```
                                          transcription
    TATA                                     start.
AAAAAGCTACTATATATAGCCTTGCATGATAGGAAACACAAATGAGTCTGTCCATCTACG
     1550      1560      1570      1580      1590      1600
```

```
    Met Ser Lys Ser Gln Leu Thr Ser Val Phe Phe Ile Leu Leu Cys Ala Leu Ser Pro
GA ATG TCT AAA TCA CAG CTA ACG TCA GTT TTC TTC ATT TTG CTT TGT GCT CTT TCA CCG
         1610        1620        1630        1640        1650

Ile Tyr Gly Ala Phe Glu Tyr Met Gln Leu Val Leu Thr Trp Pro Ile Thr Phe Cys Arg
 ATT TAT GGG GCT TTC GAG TAT ATG CAA CTC GTG TTA ACA TGG CCA ATC ACT TTT TGC CGC
         1669        1679        1689        1699        1709        1719

Ile Lys His Cys Glu Arg Thr Pro Thr Asn Phe Thr Ile His Gly Leu Trp Pro Asp Asn
 ATT AAG CAT TGC GAA AGA ACA CCA ACA AAC TTT ACG ATC CAT GGG CTT TGG CCG GAT AAC
         1729        1739        1749        1759        1769        1779

His Thr Thr Met Leu Asn Tyr Cys Asp Arg Ser Lys Pro Tyr Asn Met Phe Thr
 CAC ACC ACA ATG CTA AAT TAC TGC GAT CGC TCC AAA CCC TAT AAT ATG TTC ACG GTAAATT
         1789        1799        1809        1819        1829        1839

TCTTAGTTATTTTCCGGAGCACCTTCAAATTTTCATTTCATTTTTTCCTTTTCATTATTACTTATAAGTTTTTCCTAACG
     1850      1860      1870      1880      1890      1900      1910      1920

Asp Gly Lys Lys Lys Asn Asp Leu Asp Glu Arg Trp Pro Asp Leu Thr Lys Thr
CCAACAG GAT GGA AAA AAA AAA AAT GAT CTG GAT GAA CGC TGG CCT GAC TTG ACC AAA ACC
           1930        1940        1950        1960        1970        1980

Lys Phe Asp Ser Leu Asp Lys Gln Ala Phe Trp Lys Asp Glu Tyr Val Lys His Gly Thr
AAA TTT GAT AGT TTG GAC AAG CAA GCT TTC TGG AAA GAC GAA TAC GTA AAG CAT GGC ACG
         1991        2001        2011        2021        2031        2041

Cys Cys Ser Asp Lys Phe Asp Arg Glu Gln Tyr Phe Asp Leu Ala Met Thr Leu Arg Asp
TGT TGT TCA GAC AAG TTT GAT CGA GAG CAA TAT TTT GAT TTA GCC ATG ACA TTA AGA GAC
         2051        2061        2071        2081        2091        2101

Lys Phe Asp Leu Leu Ser Ser Leu Arg Asn His Gly Ile Ser Arg Gly Phe Ser Tyr Thr
AAG TTT GAT CTT TTG AGC TCT CTA AGA AAT CAC GGA ATT TCT CGT GGA TTT TCT TAT ACC
         2111        2121        2131        2141        2151        2161

Val Gln Asn Leu Asn Asn Thr Ile Lys Ala Ile Thr Gly Gly Phe Pro Asn Leu Thr Cys
GTT CAA AAT CTC AAT AAC ACG ATC AAG GCC ATT ACT GGA GGG TTT CCT AAT CTC ACG TGC
         2171        2181        2191        2201        2211        2221

Ser Arg Leu Arg Glu Leu Lys Glu Ile Gly Ile Cys Phe Asp Glu Thr Val Lys Asn Val
TCT AGA CTA AGG GAG CTA AAG GAG ATA GGT ATA TGT TTC GAC GAG ACG GTG AAA AAT GTG
         2231        2241        2251        2261        2271        2281

Ile Asp Cys Pro Asn Pro Lys Thr Cys Lys Pro Thr Asn Lys Gly Val Met Phe Pro ***
ATC GAT TGT CCT AAT CCT AAA ACG TGC AAA CCA ACA AAT AAG GGG GTT ATG TTT CCA TGA
         2291        2301        2311        2321        2331        2341
```

TABLE 6-continued

N. alata S₂ genomic sequence

```
TTAATAATATTTGTTTTATTGCATTATGCCATGTAAAAAAAAATTCAAAACCTCAAGTATAAACGTGTAA
    2351      2361      2371      2381      2391      2401      2411

T₁
TCAAGACTA
                                            T₂
TTAAGCACGCACTTATTGAAGACTACACTCGGAAGAATAAGCAAAATTCTTATCAATTTATGGAAATCGT
    2430      2440      2450      2460      2470      2480      2490

TATTGAACTGACGCATTCTCGTCCGTCAAATATGACATACCTTGTCAATTTTCTTCTTTATTGCCCAACA
    2500      2510      2520      2530      2540      2550      2560

TCGTATCATGATGATTGTTTACCTTAAAAATGGTAATCACAATTAGATTTGACTTTGTGGTTTTAAAAAT
    2570      2580      2590      2600      2610      2620      2630

ACGTAATTTTTTTTATGCTAGTTGTTAAGCAATAGATGGTAAGTGTAAATCAGGAAAATGAGATGAGAGC
    2640      2650      2660      2670      2680      2690      2700

TTGAGGATAGTATGTTATGCAAACCGAGTGGCACTACAAAAAATTGAAATTATTGTGGCGGCGGTACCCG
    2710      2720      2730      2740      2750      2760      2770

AGCAATATATATCAATAATACGGCGGCGTTCCAGACAACATTAGGGTATTTATGTTAAAACGGCATTTTT
    2780      2790      2800      2810      2820      2830      2840

ATAAATTATGGCGGTTCAAACGGCCACTAGTTACACAAGTTTTAAATAATTATTTGCCCTCTTTATTTGG
    2850      2860      2870      2880      2890      2900      2910

AACTCCCCCACTAATAATTTAATACTATTAAAAACATATAAAATATACTAAGCCTTCTCTAAGCCTAAAA
    2920      2930      2940      2950      2960      2970      2980

CATATGTAAACTGACGGTCTTCCCTCTCTCTATACGCCATGTCTACACCCCCTCTATCTCTCTCTCAA
    2990      3000      3010      3020      3030      3040      3050

AAACACGATTCCCCCAAATTGTTTAGCATTTATGTAAGGAGATCAGATTCCAACTCGTTTATGGTAATGT
    3060      3070      3080      3090      3100      3110      3120

GTTTGAATTC.
```

TABLE 7

Comparison of the homologous mitochondrial (Mt) sequence
with that of the upstream sequence of the S₂ gene (Nuc).[1]

```
        ———→   ———→
Nuc  ACAAAAAGTACCTATAAAAAGTATGTCCCAACAATTTAGCCTGAAATGAAAAAAAG
     *  *  * ************ ************************* *******
Mt   AGCTTGAATCCCTATAAAAAGTCCGTCCCAACAATTTAGCCTGAAAAGAAAAAAAG
             10        20        30        40        50

Nuc  TGGGGTAGAAACTAAGTTTCTTTTTAGATCCTTTTGAAATCCTCATACAACTGATGG
     **********  *   **  **  **********  *     * *  * *    *
Mt   TGGGGTAGAAGTTTCTATTGAATTGAGTAAGATCCTTTTGAATAGAAGATGCCATG
             60        70        80        90       100       110
```

[1]The S₂ gene sequence presented in this Table corresponds to the sequence of Table 6, nucleotides 1095-1206. The sequences are aligned for best overlap and homologous bases are indicated by "*." The 56bp homologous segment extends from bases 11 to 66. The two additional regions of sequence identity are underlined. The position of an 8bp direct repeat is indicated by arrows.

TABLE 8

AMINO ACID ABBREVIATIONS

| | | | | | |
|---|---|---|---|---|---|
| A = | Ala = | Alanine | M = | Met = | Methionine |
| C = | Cys = | Cysteine | N = | Asn = | Asparagine |
| D = | Asp = | Aspartic Acid | P = | Pro = | Proline |
| E = | Glu = | Glutamic Acid | Q = | Gln = | Glutamine |
| F = | Phe = | Phenylalanine | R = | Arg = | Arginine |
| G = | Gly = | Glycine | S = | Ser = | Serine |
| H = | His = | Histidine | T = | Thr = | Threonine |
| I = | Ile = | Isoleucine | V = | Val = | Valine |
| K = | Lys = | Lysine | W = | Try = | Tryptophan |
| L = | Leu = | Leucine | Y = | Tyr = | Tyrosine |

We claim:

1. A recombinant vector comprising a DNA sequence encoding an S-protein of a self-incompatible plant, wherein said self-incompatible plant displays gametophytic self-incompatability and is in the family Solanaceae.

2. A recombinant vector comprising a DNA sequence encoding an S-protein of a self-incompatible plant, wherein said self-incompatible plant displays gametophytic self-incompatibility and wherein said plant is of the genus selected from the group consisting of Nicitiana and Lycopersicon.

3. The recombinant vector of claim 2 wherein said self-incompatible plant is of the genus Nicotiana.

4. The recombinant vector of claim 3 wherein said self-incompatible plant is Nicotiana alata.

5. The recombinant vector of claim 2 wherein said DNA sequence encodes the S₂-protein of Nicotiana alata or wherein said DNA sequence is at least about 70% homologous to said DNA sequence encoding the S₂-protein of Nicotiana alata.

6. The recombinant vector of claim 2 wherein said DNA sequence encodes the $S_6$-protein of *Nicotiana alata* or wherein said DNA sequence is at least about 70% homologous to said DNA sequence encoding the $S_6$-protein of *Nicotiana alata*.

7. The recombinant vector of claim 2 wherein said DNA sequence encodes the $S_3$-protein of *Nicotiana alata* or wherein said DNA sequence is at least about 70% homologous to said DNA sequence encoding the $S_3$-protein of *Nicotiana alata*.

8. The recombinant vector of claim 2 wherein said self-incompatible plant is of the genus Lycopersicon.

9. The recombinant vector of claim 8 wherein said self-incompatible plant is *Lycopersicon peruvianum*.

10. The recombinant vector of claim 2 wherein said DNA sequence encodes the $S_1$-protein of *Lycopersicon peruvianum* or wherein said DNA sequence is at least about 70% homologous to said DNA sequence encoding the $S_1$-protein of *Lycopersicon peruvianum*.

11. The recombinant vector of claim 2 wherein said DNA sequence encodes the $S_3$-protein of *Lycopersicon peruvianum* or wherein said DNA sequence is at least about 70% homologous to said DNA sequence encoding the $S_3$-protein of *Lycopersicon peruvianum*.

12. The recombinant vector of claim 2 wherein said vector is lambda gt10.

13. The recombinant vector of claim 2 wherein the vector is M13mp8.

14. The recombinant vector of claim 1 further comprising the regulatory sequence of an S-gene of a gametophytic self-incompatible plant, said regulatory sequence directing expression of said S-protein in reproductive tissue of a gametophytic self-incompatible plant in the family Solanaceae.

15. The recombinant vector of claim 2 further comprising the regulatory sequence of an S-gene of a gametophytic self-incompatible plant said regulatory sequence directing expression of said S-protein in reproductive tissue of a gametophytic self-incompatibel plant wherein said S-gene regulatory sequence is that of a plant of a genus selected from the group consisting of Nicotiana and Lycopersicon.

16. The recombinant vector of claim 15 wherein said S-gene regulatory sequences are those of a plant of the genus Nicotiana.

17. The recombinant vector of claim 15 wherein said S-gene regulatory sequence is selected from the group consisting of that of the $S_2$-allele of *Nicotiana alata* or of an S-allele at least about 70% homologous thereto.

18. A recombinant DNA molecule comprising a DNA sequence which encodes an S-protein of a gametophytic self-incompatible plant in the family Solanaceae.

19. A recombinant DNA molecule comprising a DNA sequence which encodes an S-protein of a gameotphytic self-incompatible plant, wherein said plant is of a genus selected from the group consisting of Nicotiana and Lycopersicon.

20. The recombinant DNA molecule of claim 19 wherein said self-incompatible plant is of the genus Nicotiana.

21. The recombinant DNA molecule of claim 20 wherein said self-incompatible plant is *Nicotiana alata*.

22. The recombinant DNA molecule of claim 19 wherein said DNA sequence encodes the $S_2$-protein of *Nicotiana alata* or wherein said DNA sequence is at least about 70% homologous to said DNA sequence encoding the $S_2$-protein of *Nicotiana alata*.

23. The recombinant DNA molecule of claim 19 wherein said DNA sequence encodes the $S_3$-protein of *Nicotiana alata* or wherein said DNA sequence is at least about 70% homologous to said DNA sequence encoding the $S_3$-protein of *Nicotiana alata*.

24. The recombinant DNA molecule of claim 19 wherein said DNA sequence encodes the $S_6$-protein of *Nicotiana alata* or wherein said DNA sequence is at least about 70% homologous to said DNA sequence encoding the $S_6$-protein of *Nicotiana alata*.

25. The recombinant DNA molecule of claim 19 wherein said self-incompatible plant is of the genus Lycopersicon.

26. The recombinant DNA molecule of claim 25 wherein said self-incompatible plant is *Lycopersicon peruvianum*.

27. The recombinant DNA molecule of claim 19 wherein said DNA sequence encodes the $S_1$-protein of *Lycopersicon peruvianum* or wherein said DNA sequence is at least about 70% homologous to said DNA sequence encoding the $S_1$-protein of *Lycopersicon peruvianum*.

28. The recombinant DNA molecule of claim 19 wherein said DNA sequence encodes the $S_3$-protein of *Lycopersicon peruvianum* or wherein said DNA sequence is at least about 70% homologous to said DNA sequence encoding the $S_3$-protein of *Lycopersicon peruvianum*.

29. The recombinant DNA molecule of claim 19 which further comprises the regulatory sequences of the $S_2$-allele of *Nicotiana alata*.

30. A recombinant DNA molecule comprising a DNA sequence which encodes a signal sequence of an S-protein of a gametophytic self-incompatible plant in the family Solanaceae.

31. A recombinant DNA molecule comprising a DNA sequence which encodes a signal sequence of an S-protein of a gametophytic self-incompatible plant wherein said S-protein is of a plant of a genus selected from the group consisting of Nicotiana and Lycopersicon.

32. The recombinant DNA molecule of claim 31 wherein said signal sequence is that of an S-protein of *Nicotiana alata*.

33. The recombinant DNA molecule of claim 31 wherein said signal sequence is encoded within the $S_2$-gene of *Nicotiana alata* or within an S-gene at least about 70% homologous thereto.

34. The recombinant molecule of claim 31 wherein the signal sequence is encoded by DNA comprising the nucleotide sequence 5'-ATG TCT AAA TCA CAG CTA ACG TCA GTT TTC TTC ATT TTG CTT TGT GCT CTT TCA CCG ATT TAT GGG-3'.

35. A recombinant DNA molecule which comprises the regulatory sequence of an S-gene of a gametophytic self-incompatible plant, said regulatory sequence capable of directing expression of a heterologous structural gene placed under its regulatory control in reproductive tissue of a gametophytic self-incompatible plant in the family Solanaceae.

36. A recombinant DNA molecule which comprises the regulatory sequence of an S-gene of a gametophytic self-incompatible plant, said regulatory sequence capable of directing expression of a heterologous structural gene placed under its regulatory control in reproductive tissue of a gametophytic self-incompatible plant wherein said S-gene is of a plant of a genus selected from the group consisting of Nicotiana and Lycopersicon.

37. The recombinant DNA molecule of claim 36 wherein said regulatory sequence directs gene expression in female secretory tissue of a gametophytic self-incompatible plant.

38. The recombinant DNA molecule of claim 36 wherein said regulatory sequence directs gene expression in pollen of a gametophytic self-incompatible plant.

39. The recombinant DNA molecule of claim 36 wherein said regulatory sequence is that of an S-allele of a self-incompatible plant of the genus Nicotiana.

40. The recombinant DNA molecule of claim 39 wherein said regulatory sequence is that of the S-allele of *Nicotiana alata*.

41. The recombinant DNA molecule of claim 36 wherein the S-allele is the $S_2$-allele of *Nicotiana alata* or is at least about 70% homologous thereto.

42. The recombinant DNA molecule of claim 35 further comprising a plant-expressible structural gene placed under the regulatory control of said regulatory sequence wherein said structural gene does not encode an S-protein of a gametophytic self-incompatible plant in the family Solanaceae.

43. The recombinant DNA molecule of claim 36 further comprising a plant-expressible structural gene placed under the regulatory control of said regulatory sequence wherein said structural gene does not encode an S-protein of a plant of a genus selected form the group consisting of Nicotiana and Lycopersicon.

44. The recombinant DNA molecule of claim 43 in which said plant expressible structural gene comprises a signal sequence of an S-gene of a plant of a genus selected from the group consisting of Nicotiana and Lycopersicon.

* * * * *

UNITED STATES PATENT AND TRADEMARK OFFICE
CERTIFICATE OF CORRECTION

PATENT NO. : 5,053,331                    Page 1 of 11

DATED       : Oct. 1, 1991

INVENTOR(S) : Adrienne Clarke, et al

It is certified that error appears in the above-identified patent and that said Letters Patent is hereby corrected as shown below:

On the Cover page, in item 75, please delete "Robert Bernatzky, New Salem, Mass."

In drawing Figs. delete Figure 1, and replace it with the attached copy of Figure 1.

At column 1, line 5, please add after "1986," and before "which," --now abandoned,--.

At column 1, line 34, please rewrite "$N$" as --$N.$--.

At column 2, bridging lines 11 and 12, please rewrite "In alata" as --In $N.$ $alata$--.

At column 2, line 21, please rewrite "in vitro" as --$in$ $vitro$--.

At column 2, line 65, please rewrite "$s_2s_2$" as --$S_2S_2$--.

At column 3, line 18, please rewrite "in vitro" as --$in$ $vitro$--.

At column 3, bridging lines 33 and 34, please rewrite "N-ter-,oma;" as --N-terminal--.

Col. 3, line 34, "N. a;lata" should read --N. alata--

At column 3, line 53, please rewrite "50:136501367;" as --50:1365-1367;--.

At column 4, line 36, please rewrite "sequences," as --sequences--.

UNITED STATES PATENT AND TRADEMARK OFFICE
CERTIFICATE OF CORRECTION

PATENT NO. : 5,053,331                                                    Page 2 of 11

DATED : Oct. 1, 1991

INVENTOR(S) : Adrienne Clarke, et al

It is certified that error appears in the above-identified patent and that said Letters Patent is hereby corrected as shown below:

At column 4, line 47, please rewrite "Nicotiana" as --*Nicotiana*--.

At column 4, line 53, please rewrite "general" as --genera--.

At column 4, line 53, please rewrite "Nicotiana and Lycopersicon" as --*Nicotiana* and *Lycopersicon*--.

At column 4, line 61, please rewrite "method" as --methods--.

At column 4, line 64, please rewrite "clones" as --clones,--.

At column 4, line 65, please rewrite "herein" as --herein,--.

At column 4, line 68, please rewrite "extra cellular" as --extracellular--.

At column 5, line 5, please rewrite "in vivo" as --*in vivo*--.

At column 6, line 53, please rewrite "mollecular" as --molecular--.

At column 6, line 53, please rewrite "in vitro" as --*in vitro*--.

At column 7, line 21, please rewrite "HindIII" as --*Hin*dIII--.

UNITED STATES PATENT AND TRADEMARK OFFICE
CERTIFICATE OF CORRECTION

PATENT NO. : 5,053,331

DATED : Oct. 1, 1991

INVENTOR(S) : Adrienne Clarke, et al

It is certified that error appears in the above-identified patent and that said Letters Patent is hereby corrected as shown below:

At column 7, line 35, please rewrite "HindIII" as --*Hind*III--.

At column 7, line 60, please rewrite "in vitro" as --*in vitro*--.

At column 9, line 52, please rewrite "in vitro" as --*in vitro*--.

At column 9, line 53, please rewrite "*clonging*" as --*cloning*--.

At column 10, bridging lines 25 and 26, please rewrite "degenerate" as --degenerate,--.

At column 11, line 40, please rewrite "indicted" as --indicated--.

At column 12, line 5, please rewrite "Brassica" as --*Brassica*--.

At column 12, line 6, please rewrite "isolated" as --isolated,--.

At column 12, line 25, please rewrite "S2" as --$S_2$--.

At column 12, line 35, please rewrite "in vitro" as --*in vitro*--.

UNITED STATES PATENT AND TRADEMARK OFFICE
CERTIFICATE OF CORRECTION

PATENT NO. : 5,053,331

DATED : Oct. 1, 1991

INVENTOR(S) : Adrienne Clarke, et al

Page 4 of 11

It is certified that error appears in the above-identified patent and that said Letters Patent is hereby corrected as shown below:

At column 12, line 68, please rewrite "32P-labelled" as --$^{32}$P-labelled--.

At column 14, line 33, please rewrite "differnoes" as --differences--.

At column 15, line 20, please delete the second --alleles--.

At column 15, line 21, please rewrite "Brassica" as --*Brassica*--.

At column 16, line 65, please rewrite "1603 2338" as --1603-2338--.

At column 18, line 17, please rewrite "L. esculentum" as --*L. esçulentum,*--.

At column 18, line 27, please rewrite "indivudal" as --individual--.

At column 18, line 61, please rewrite "in vitro" as --*in vitro*--.

At column 19, line 25, please rewrite "Reglated" as --Regulated--.

At column 19, line 27, please rewrite "In situ" as --*In situ*--.

At column 19, line 32, please rewrite "in situ" as --*in situ*--.

UNITED STATES PATENT AND TRADEMARK OFFICE
CERTIFICATE OF CORRECTION

PATENT NO. : 5,053,331

DATED : Oct. 1, 1991

INVENTOR(S) : Adrienne Clarke, et al

It is certified that error appears in the above-identified patent and that said Letters Patent is hereby corrected as shown below:

At column 20, line 2, please rewrite "stigma" as --stigmas--.

At column 20, line 4, please rewrite "stigma" as --stigmas--.

At column 20, line 25, please delete "Cl".

At column 20, lines 25 and 26, "Example 2: Purification of 32K $S_2$-protein from *Nicotiana alata* styles" should be a new paragraph heading.

At column 20, line 42, please rewrite "CaCl2" as --$CaCl_2$--.

At column 20, line 61, please rewrite "MgCl2," as --$MgCl_2$,--.

At column 21, line 19, please rewrite "methyl-α-Dman-" as --methyl-α-D-man---.

At column 21, line 28, please rewrite "methyl-o-D-mannoside." as --methyl-α-D-mannoside.--.

At column 21, line 58, please rewrite "in vitro" as --*in vitro*--.

At column 22, line 14, please rewrite "H2O" as --$H_2O$--.

At column 22, line 55, please rewrite "(Huynh et al., 1985, supra)." as --Huynh *et al.*, (1985, *supra*).--.

UNITED STATES PATENT AND TRADEMARK OFFICE
CERTIFICATE OF CORRECTION

PATENT NO. : 5,053,331

DATED : Oct. 1, 1991

INVENTOR(S) : Adrienne Clarke, et al

It is certified that error appears in the above-identified patent and that said Letters Patent is hereby corrected as shown below:

At column 22, line 65, please delete the "i" after infect.

At column 22, line 65, please rewrite "E. coli" as --*E. coli*--.

At column 23, line 38, please rewrite "MgCl2," as --$MgCl_2$--.

At column 23, line 49, please rewrite "products" as --products.--.

At column 23, line 54, please rewrite "37" as --37°--.

At column 24, line 57, please rewrite "42." as --42°--.

At column 24, line 65, please delete "The" after "0.25 µg". and "in vacuo" should read --*in vacuo*--

At column 25, line 4, please rewrite "in vacuo" as --*in vacuo*--.

Column 25, line 43, "in" should read --is--

At column 25, line 55, please rewrite "necleotides" as --nucleotides--.

At column 25, line 61, please rewrite "$^{32}$-P-labelled" as --$^{32}$P-labelled--.

At column 26, line 9, please rewrite "$S_3$-allele" as --$S_3$-allele,--.

UNITED STATES PATENT AND TRADEMARK OFFICE
CERTIFICATE OF CORRECTION

PATENT NO. : 5,053,331

DATED : Oct. 1, 1991

INVENTOR(S) : Adrienne Clarke, et al

It is certified that error appears in the above-identified patent and that said Letters Patent is hereby corrected as shown below:

At column 26, line 10, please rewrite "selecteed" as --selected--.

At column 26, line 33, please rewrite "suora" as --*supra*--.

At column 26, line 43, please rewrite "Which" as --which--.

At column 28, line 16, please rewrite "Filtes" as --Filters--.

At columns 29 and 30, Table 3-continued, fourth line of the nucleic acid sequence, please rewrite the last codon "AAC" as --AAG--.

At columns 31 and 32, Table 5, line 1 of the nucleic acid sequence, between nucleic acids 39 and 44, please rewrite "TTTTTT" as --TTTTT--.

At columns 35 and 36, Table 6-continued, second line of the nucleic acid sequence, please terminate the arrow over nucleic acid number 1187 instead of nucleic acid number 1188.

At columns 35 and 36, Table 6-continued, sixth line of the nucleic acid sequence at nucleic acid positions 1429-1431, please rewrite "ACT" as --AGT--.

At columns 37 and 38, Table 7, please delete the "*" associated with nucleic acid position number 47.

UNITED STATES PATENT AND TRADEMARK OFFICE
CERTIFICATE OF CORRECTION

PATENT NO. : 5,053,331

DATED : Oct. 1, 1991

INVENTOR(S) : Adrienne Clarke, et al

It is certified that error appears in the above-identified patent and that said Letters Patent is hereby corrected as shown below:

At columns 37 and 38, Table 7, line 2 of the $S_2$ nucleic acid sequence, please rewrite "AAGTTTCT" as --AAGTTTCT--.

At columns 37 and 38, Table 7, line 2 of the $S_2$ nucleic acid sequence, please rewrite "AGATCCTTTTGAA" as --AGATCCTTTTGAA--.

At column 38, claim 2, line 59, please rewrite "Nicitiana" as --Nicotiana--.

At column 38, claim 2, line 59, please rewrite "Lycopersicon" as --Lycopersicon--.

At column 38, claim 3, line 61, please rewrite "Nicotiana" as --Nicotiana--.

At column 39, claim 8, line 12, please rewrite "Lycopersicon" as --Lycopersicon--.

At column 39, claim 15, line 39, please rewrite "self-incompatibel" as --self-incompatible--.

At column 39, claim 15, line 42, please rewrite "Nicotiana and Lycopersicon" as --Nicotiana and Lycopersicon--.

At column 39, claim 16, line 45, please rewrite "Nicotiana" as --Nicotiana--.

At column 39, claim 19, bridging lines 55 and 56, please rewrite "gameotphytic" as --gametophytic--.

UNITED STATES PATENT AND TRADEMARK OFFICE
CERTIFICATE OF CORRECTION

PATENT NO. : 5,053,331

DATED : Oct. 1, 1991

INVENTOR(S) : Adrienne Clarke, et al

It is certified that error appears in the above-identified patent and that said Letters Patent is hereby corrected as shown below:

At column 39, claim 19, bridging lines 57 and 58, please rewrite "Nicotiana and Lycopersicon" as --*Nicotiana* and *Lycopersicon*--.

At column 39, claim 20, line 61, please rewrite "Nicotiana" as --*Nicotiana*--.

At column 40, claim 31, bridging lines 41 and 42, please rewrite "Nicotiana and Lycopersicon" as --*Nicotiana* and *Lycopersicon*--.

At column 41, claim 36, bridging lines 1 and 2, please rewrite "Nicotiana and Lycopersicon" as --*Nicotiana* and *Lycopersicon*--.

At column 41, claim 39, line 12, please rewrite "Nicotiana" as --*Nicotiana*--.

At column 42, claim 43, line 11, please rewrite "form" as --from--.

UNITED STATES PATENT AND TRADEMARK OFFICE
CERTIFICATE OF CORRECTION

PATENT NO. : 5,053,331

DATED : Oct. 1, 1991

INVENTOR(S) : Adrienne Clarke, et al

It is certified that error appears in the above-identified patent and that said Letters Patent is hereby corrected as shown below:

At column 42, claim 43, line 12, please rewrite "Nicotiana and Lycopersicon" as --*Nicotiana* and *Lycopersicon*--.

At column 42, claim 44, bridging lines 16 and 17, please rewrite "Nicotiana and Lycopersicon" as --*Nicotiana* and *Lycopersicon*--.

Signed and Sealed this

Fourteenth Day of June, 1994

Attest:

BRUCE LEHMAN

*Attesting Officer*          Commissioner of Patents and Trademarks